United States Patent
Xiong et al.

(10) Patent No.: US 8,204,297 B1
(45) Date of Patent: Jun. 19, 2012

(54) METHODS AND SYSTEMS FOR CLASSIFYING DEFECTS DETECTED ON A RETICLE

(75) Inventors: Yalin Xiong, Union City, CA (US); Carl Hess, Los Altos, CA (US)

(73) Assignee: KLA-Tencor Corp., San Jose, CA (US)

( * ) Notice: Subject to any disclaimer, the term of this patent is extended or adjusted under 35 U.S.C. 154(b) by 553 days.

(21) Appl. No.: 12/394,752

(22) Filed: Feb. 27, 2009

(51) Int. Cl.
*G06K 9/00* (2006.01)
*G01N 21/00* (2006.01)

(52) U.S. Cl. .............. 382/149; 356/237.4; 702/108
(58) Field of Classification Search .......... 382/144–154; 356/237.1–237.5; 702/108
See application file for complete search history.

(56) References Cited

U.S. PATENT DOCUMENTS

| | | |
|---|---|---|
| 3,495,269 A | 2/1970 | Mutschler et al. |
| 3,496,352 A | 2/1970 | Jugle |
| 3,909,602 A | 9/1975 | Micka |
| 4,015,203 A | 3/1977 | Verkuil |
| 4,247,203 A | 1/1981 | Levy et al. |
| 4,347,001 A | 8/1982 | Levy et al. |
| 4,378,159 A | 3/1983 | Galbraith |
| 4,448,532 A | 5/1984 | Joseph et al. |
| 4,532,650 A | 7/1985 | Wihl et al. |
| 4,555,798 A | 11/1985 | Broadbent, Jr. et al. |
| 4,578,810 A | 3/1986 | MacFarlane et al. |
| 4,579,455 A | 4/1986 | Levy et al. |
| 4,595,289 A | 6/1986 | Feldman et al. |
| 4,599,558 A | 7/1986 | Castellano et al. |
| 4,633,504 A | 12/1986 | Wihl |
| 4,641,353 A | 2/1987 | Kobayashi |
| 4,641,967 A | 2/1987 | Pecen |
| 4,734,721 A | 3/1988 | Boyer et al. |
| 4,748,327 A | 5/1988 | Shinozaki et al. |
| 4,758,094 A | 7/1988 | Wihl |
| 4,766,324 A | 8/1988 | Saadat et al. |
| 4,799,175 A | 1/1989 | Sano et al. |
| 4,805,123 A | 2/1989 | Specht et al. |
| 4,812,756 A | 3/1989 | Curtis et al. |
| 4,814,829 A | 3/1989 | Kosugi et al. |
| 4,817,123 A | 3/1989 | Sones et al. |
| 4,845,558 A | 7/1989 | Tsai et al. |
| 4,877,326 A | 10/1989 | Chadwick et al. |

(Continued)

FOREIGN PATENT DOCUMENTS

EP 0032197 7/1981

(Continued)

OTHER PUBLICATIONS

Allan et al., "Critical Area Extraction for Soft Fault Estimation," IEEE Transactions on Semiconductor Manufacturing, vol. 11, No. 1, Feb. 1998.

(Continued)

*Primary Examiner* — Hoa Pham
(74) *Attorney, Agent, or Firm* — Ann Marie Mewherter

(57) ABSTRACT

Methods and systems for classifying defects detected on a reticle are provided. One method includes determining an impact that a defect detected on a reticle will have on the performance of a device being fabricated on a wafer based on how at least a portion of the reticle prints or will print on the wafer. The defect is located in the portion of the reticle. The method also includes assigning a classification to the defect based on the impact.

19 Claims, 4 Drawing Sheets

U.S. PATENT DOCUMENTS

| | | | |
|---|---|---|---|
| 4,926,489 A | 5/1990 | Danielson et al. |
| 4,928,313 A | 5/1990 | Leonard et al. |
| 5,046,109 A | 9/1991 | Fujimori et al. |
| 5,124,927 A | 6/1992 | Hopewell et al. |
| 5,189,481 A | 2/1993 | Jann et al. |
| 5,355,212 A | 10/1994 | Wells et al. |
| 5,444,480 A | 8/1995 | Sumita |
| 5,453,844 A | 9/1995 | George et al. |
| 5,459,520 A | 10/1995 | Sasaki |
| 5,481,624 A | 1/1996 | Kamon |
| 5,485,091 A | 1/1996 | Verkuil |
| 5,497,381 A | 3/1996 | O'Donoghue et al. |
| 5,528,153 A | 6/1996 | Taylor et al. |
| 5,544,256 A | 8/1996 | Brecher et al. |
| 5,563,702 A | 10/1996 | Emery et al. |
| 5,572,598 A | 11/1996 | Wihl et al. |
| 5,578,821 A | 11/1996 | Meisberger et al. |
| 5,594,247 A | 1/1997 | Verkuil et al. |
| 5,608,538 A | 3/1997 | Edger et al. |
| 5,619,548 A | 4/1997 | Koppel |
| 5,621,519 A | 4/1997 | Frost et al. |
| 5,644,223 A | 7/1997 | Verkuil |
| 5,650,731 A | 7/1997 | Fung |
| 5,661,408 A | 8/1997 | Kamieniecki et al. |
| 5,689,614 A | 11/1997 | Gronet et al. |
| 5,694,478 A | 12/1997 | Braier et al. |
| 5,696,835 A | 12/1997 | Hennessey et al. |
| 5,703,969 A | 12/1997 | Hennessey et al. |
| 5,737,072 A | 4/1998 | Emery et al. |
| 5,742,658 A | 4/1998 | Tiffin et al. |
| 5,754,678 A | 5/1998 | Hawthorne et al. |
| 5,767,691 A | 6/1998 | Verkuil |
| 5,767,693 A | 6/1998 | Verkuil |
| 5,771,317 A | 6/1998 | Edgar |
| 5,773,989 A | 6/1998 | Edelman et al. |
| 5,774,179 A | 6/1998 | Chevrette et al. |
| 5,795,685 A | 8/1998 | Liebmann et al. |
| 5,822,218 A | 10/1998 | Moosa et al. |
| 5,831,865 A * | 11/1998 | Berezin et al. ............... 382/149 |
| 5,834,941 A | 11/1998 | Verkuil |
| 5,852,232 A | 12/1998 | Samsavar et al. |
| 5,866,806 A | 2/1999 | Samsavar et al. |
| 5,874,733 A | 2/1999 | Silver et al. |
| 5,884,242 A | 3/1999 | Meier et al. |
| 5,889,593 A | 3/1999 | Bareket |
| 5,917,332 A | 6/1999 | Chen et al. |
| 5,932,377 A | 8/1999 | Ferguson et al. |
| 5,940,458 A | 8/1999 | Suk |
| 5,948,972 A | 9/1999 | Samsavar et al. |
| 5,955,661 A | 9/1999 | Samsavar et al. |
| 5,965,306 A | 10/1999 | Mansfield et al. |
| 5,978,501 A | 11/1999 | Badger et al. |
| 5,980,187 A | 11/1999 | Verhovsky |
| 5,986,263 A | 11/1999 | Hiroi et al. |
| 5,991,699 A | 11/1999 | Kulkarni et al. |
| 5,999,003 A | 12/1999 | Steffan et al. |
| 6,011,404 A | 1/2000 | Ma et al. |
| 6,014,461 A | 1/2000 | Hennessey et al. |
| 6,040,912 A | 3/2000 | Zika et al. |
| 6,052,478 A | 4/2000 | Wihl et al. |
| 6,060,709 A | 5/2000 | Verkuil et al. |
| 6,072,320 A | 6/2000 | Verkuil |
| 6,076,465 A | 6/2000 | Vacca et al. |
| 6,078,738 A | 6/2000 | Garza et al. |
| 6,091,257 A | 7/2000 | Verkuil et al. |
| 6,091,846 A | 7/2000 | Lin et al. |
| 6,097,196 A | 8/2000 | Verkuil et al. |
| 6,097,887 A | 8/2000 | Hardikar et al. |
| 6,104,206 A | 8/2000 | Verkuil |
| 6,104,835 A | 8/2000 | Han |
| 6,117,598 A | 9/2000 | Imai |
| 6,121,783 A | 9/2000 | Horner et al. |
| 6,122,017 A | 9/2000 | Taubman |
| 6,122,046 A | 9/2000 | Almogy |
| 6,137,570 A | 10/2000 | Chuang et al. |
| 6,141,038 A | 10/2000 | Young et al. |
| 6,146,627 A | 11/2000 | Muller |
| 6,171,737 B1 | 1/2001 | Phan et al. |
| 6,175,645 B1 | 1/2001 | Elyasaf et al. |
| 6,184,929 B1 | 2/2001 | Noda et al. |
| 6,184,976 B1 | 2/2001 | Park et al. |
| 6,191,605 B1 | 2/2001 | Miller et al. |
| 6,201,999 B1 | 3/2001 | Jevtic |
| 6,202,029 B1 | 3/2001 | Verkuil et al. |
| 6,205,239 B1 | 3/2001 | Lin et al. |
| 6,224,638 B1 | 5/2001 | Jevtic et al. |
| 6,233,719 B1 | 5/2001 | Hardikar et al. |
| 6,246,787 B1 | 6/2001 | Hennessey et al. |
| 6,248,485 B1 | 6/2001 | Cuthbert |
| 6,248,486 B1 | 6/2001 | Dirksen et al. |
| 6,259,960 B1 | 7/2001 | Inokuchi |
| 6,266,437 B1 | 7/2001 | Eichel et al. |
| 6,267,005 B1 | 7/2001 | Samsavar et al. |
| 6,268,093 B1 | 7/2001 | Kenan et al. |
| 6,272,236 B1 | 8/2001 | Pierrat et al. |
| 6,282,309 B1 | 8/2001 | Emery |
| 6,292,582 B1 | 9/2001 | Lin et al. |
| 6,324,298 B1 | 11/2001 | O'Dell et al. |
| 6,344,640 B1 | 2/2002 | Rhoads |
| 6,363,166 B1 | 3/2002 | Wihl et al. |
| 6,373,975 B1 | 4/2002 | Bula et al. |
| 6,388,747 B2 | 5/2002 | Nara et al. |
| 6,393,602 B1 | 5/2002 | Atchison et al. |
| 6,415,421 B2 | 7/2002 | Anderson et al. |
| 6,445,199 B1 | 9/2002 | Satya et al. |
| 6,451,690 B1 | 9/2002 | Matsumoto |
| 6,466,314 B1 | 10/2002 | Lehman |
| 6,466,315 B1 | 10/2002 | Karpol et al. |
| 6,470,489 B1 | 10/2002 | Chang et al. |
| 6,483,938 B1 | 11/2002 | Hennessey et al. |
| 6,513,151 B1 | 1/2003 | Erhardt et al. |
| 6,526,164 B1 | 2/2003 | Mansfield et al. |
| 6,529,621 B1 | 3/2003 | Glasser et al. |
| 6,535,628 B2 | 3/2003 | Smargiassi et al. |
| 6,539,106 B1 | 3/2003 | Gallarda et al. |
| 6,569,691 B1 | 5/2003 | Jastrzebski et al. |
| 6,581,193 B1 | 6/2003 | McGhee et al. |
| 6,593,748 B1 | 7/2003 | Halliyal et al. |
| 6,597,193 B2 | 7/2003 | Lagowski et al. |
| 6,602,728 B1 | 8/2003 | Liebmann et al. |
| 6,608,681 B2 | 8/2003 | Tanaka et al. |
| 6,614,520 B1 | 9/2003 | Bareket et al. |
| 6,631,511 B2 | 10/2003 | Haffner |
| 6,636,301 B1 | 10/2003 | Kvamme et al. |
| 6,642,066 B1 | 11/2003 | Halliyal et al. |
| 6,658,640 B2 | 12/2003 | Weed |
| 6,665,065 B1 | 12/2003 | Phan et al. |
| 6,670,082 B2 | 12/2003 | Liu et al. |
| 6,680,621 B2 | 1/2004 | Savtchouk et al. |
| 6,691,052 B1 | 2/2004 | Maurer |
| 6,701,004 B1 | 3/2004 | Shykind et al. |
| 6,718,526 B1 | 4/2004 | Eldredge et al. |
| 6,721,695 B1 | 4/2004 | Chen et al. |
| 6,734,696 B2 | 5/2004 | Horner et al. |
| 6,738,954 B1 | 5/2004 | Allen et al. |
| 6,748,103 B2 | 6/2004 | Glasser |
| 6,751,519 B1 | 6/2004 | Satya et al. |
| 6,753,954 B2 | 6/2004 | Chen |
| 6,757,645 B2 | 6/2004 | Chang |
| 6,759,655 B2 | 7/2004 | Nara et al. |
| 6,771,806 B1 | 8/2004 | Satya et al. |
| 6,775,818 B2 | 8/2004 | Taravade et al. |
| 6,777,147 B1 | 8/2004 | Fonseca et al. |
| 6,777,676 B1 | 8/2004 | Wang et al. |
| 6,778,695 B1 | 8/2004 | Schellenberg et al. |
| 6,779,159 B2 | 8/2004 | Yokoyama et al. |
| 6,784,446 B1 | 8/2004 | Phan et al. |
| 6,788,400 B2 | 9/2004 | Chen |
| 6,789,032 B2 | 9/2004 | Barbour et al. |
| 6,803,554 B2 | 10/2004 | Ye et al. |
| 6,806,456 B1 | 10/2004 | Ye et al. |
| 6,807,503 B2 | 10/2004 | Ye et al. |
| 6,813,572 B2 | 11/2004 | Satya et al. |
| 6,820,028 B2 | 11/2004 | Ye et al. |
| 6,828,542 B2 | 12/2004 | Ye et al. |
| 6,842,225 B1 | 1/2005 | Irie |
| 6,859,746 B1 | 2/2005 | Stirton |

| Patent | Date | Inventor |
|---|---|---|
| 6,879,924 B2 | 4/2005 | Ye et al. |
| 6,882,745 B2 | 4/2005 | Brankner |
| 6,884,984 B2 | 4/2005 | Ye et al. |
| 6,886,153 B1 | 4/2005 | Bevis |
| 6,892,156 B2 | 5/2005 | Ye et al. |
| 6,902,855 B2 | 6/2005 | Peterson et al. |
| 6,906,305 B2 | 6/2005 | Pease et al. |
| 6,918,101 B1 | 7/2005 | Satya et al. |
| 6,937,753 B1 | 8/2005 | O'Dell et al. |
| 6,948,141 B1 | 9/2005 | Satya et al. |
| 6,959,255 B2 | 10/2005 | Ye et al. |
| 6,966,047 B1 | 11/2005 | Glasser |
| 6,969,837 B2 | 11/2005 | Ye et al. |
| 6,969,864 B2 | 11/2005 | Ye et al. |
| 6,983,060 B1 | 1/2006 | Martinent-Catalot et al. |
| 6,988,045 B2 | 1/2006 | Purdy |
| 7,003,755 B2 | 2/2006 | Pang et al. |
| 7,003,758 B2 | 2/2006 | Ye et al. |
| 7,012,438 B1 | 3/2006 | Miller et al. |
| 7,026,615 B2 | 4/2006 | Takane et al. |
| 7,027,143 B1 | 4/2006 | Stokowski et al. |
| 7,030,966 B2 | 4/2006 | Hansen |
| 7,030,997 B2 | 4/2006 | Neureuther et al. |
| 7,053,355 B2 | 5/2006 | Ye et al. |
| 7,061,625 B1 | 6/2006 | Hwang |
| 7,071,833 B2 | 7/2006 | Nagano et al. |
| 7,103,484 B1 | 9/2006 | Shi et al. |
| 7,106,895 B1 | 9/2006 | Goldberg et al. |
| 7,107,517 B1 | 9/2006 | Suzuki et al. |
| 7,107,571 B2 | 9/2006 | Chang et al. |
| 7,111,277 B2 | 9/2006 | Ye et al. |
| 7,114,143 B2 | 9/2006 | Hanson et al. |
| 7,114,145 B2 | 9/2006 | Ye et al. |
| 7,117,477 B2 | 10/2006 | Ye et al. |
| 7,117,478 B2 | 10/2006 | Ye et al. |
| 7,120,285 B1 | 10/2006 | Spence |
| 7,120,895 B2 | 10/2006 | Ye et al. |
| 7,123,356 B1 | 10/2006 | Stokowski |
| 7,124,386 B2 | 10/2006 | Smith |
| 7,133,548 B2 | 11/2006 | Kenan et al. |
| 7,135,344 B2 | 11/2006 | Nehmadi |
| 7,136,143 B2 | 11/2006 | Smith |
| 7,152,215 B2 | 12/2006 | Smith |
| 7,162,071 B2 | 1/2007 | Hung et al. |
| 7,171,334 B2 | 1/2007 | Gassner |
| 7,174,520 B2 | 2/2007 | White |
| 7,194,709 B2 | 3/2007 | Brankner |
| 7,207,017 B1 | 4/2007 | Tabery et al. |
| 7,231,628 B2 | 6/2007 | Pack et al. |
| 7,236,847 B2 | 6/2007 | Marella |
| 7,271,891 B1 * | 9/2007 | Xiong et al. ........... 356/237.4 |
| 7,379,175 B1 * | 5/2008 | Stokowski et al. ...... 356/237.5 |
| 7,383,156 B2 | 6/2008 | Matsusita et al. |
| 7,386,839 B1 | 6/2008 | Golender et al. |
| 7,418,124 B2 | 8/2008 | Peterson et al. |
| 7,424,145 B2 | 9/2008 | Horie et al. |
| 7,440,093 B1 * | 10/2008 | Xiong et al. ........... 356/237.4 |
| 7,676,077 B2 | 3/2010 | Kulkarni et al. |
| 7,738,093 B2 * | 6/2010 | Alles et al. ............ 356/237.5 |
| 7,739,064 B1 | 6/2010 | Ryker et al. |
| 2001/0019625 A1 | 9/2001 | Kenan et al. |
| 2001/0022858 A1 | 9/2001 | Komiya et al. |
| 2001/0043735 A1 | 11/2001 | Smargiassi et al. |
| 2002/0019729 A1 | 2/2002 | Chang et al. |
| 2002/0026626 A1 | 2/2002 | Randall et al. |
| 2002/0033449 A1 | 3/2002 | Nakasuji et al. |
| 2002/0035461 A1 | 3/2002 | Chang et al. |
| 2002/0035641 A1 | 3/2002 | Kurose |
| 2002/0088951 A1 | 7/2002 | Chen |
| 2002/0090746 A1 | 7/2002 | Xu et al. |
| 2002/0134936 A1 | 9/2002 | Matsui et al. |
| 2002/0144230 A1 | 10/2002 | Rittman |
| 2002/0164065 A1 | 11/2002 | Cai et al. |
| 2002/0176096 A1 | 11/2002 | Sentoku et al. |
| 2002/0181756 A1 | 12/2002 | Shibuya et al. |
| 2002/0186878 A1 | 12/2002 | Hoon et al. |
| 2002/0192578 A1 | 12/2002 | Tanaka et al. |
| 2003/0014146 A1 | 1/2003 | Fujii |
| 2003/0017664 A1 | 1/2003 | Pnueli et al. |
| 2003/0022401 A1 | 1/2003 | Hamamatsu et al. |
| 2003/0033046 A1 | 2/2003 | Yoshitake et al. |
| 2003/0048458 A1 | 3/2003 | Mieher |
| 2003/0048939 A1 | 3/2003 | Lehman |
| 2003/0057971 A1 | 3/2003 | Nishiyama et al. |
| 2003/0086081 A1 | 5/2003 | Lehman |
| 2003/0094572 A1 | 5/2003 | Matsui et al. |
| 2003/0098805 A1 | 5/2003 | Bizjak |
| 2003/0128870 A1 | 7/2003 | Pease et al. |
| 2003/0138138 A1 | 7/2003 | Vacca et al. |
| 2003/0138978 A1 | 7/2003 | Tanaka et al. |
| 2003/0169916 A1 | 9/2003 | Hayashi et al. |
| 2003/0207475 A1 | 11/2003 | Nakasuji et al. |
| 2003/0223639 A1 | 12/2003 | Shlain et al. |
| 2003/0226951 A1 | 12/2003 | Ye et al. |
| 2003/0228714 A1 | 12/2003 | Smith |
| 2003/0229410 A1 | 12/2003 | Smith |
| 2003/0229412 A1 | 12/2003 | White |
| 2003/0229868 A1 | 12/2003 | White |
| 2003/0229875 A1 | 12/2003 | Smith |
| 2003/0229880 A1 | 12/2003 | White |
| 2003/0229881 A1 | 12/2003 | White |
| 2003/0237064 A1 | 12/2003 | White et al. |
| 2004/0030430 A1 | 2/2004 | Matsuoka |
| 2004/0032908 A1 | 2/2004 | Hagai et al. |
| 2004/0049722 A1 | 3/2004 | Matsushita |
| 2004/0052411 A1 | 3/2004 | Qian et al. |
| 2004/0057611 A1 | 3/2004 | Peterson et al. |
| 2004/0091142 A1 | 5/2004 | Peterson et al. |
| 2004/0094762 A1 | 5/2004 | Hess et al. |
| 2004/0098216 A1 | 5/2004 | Ye et al. |
| 2004/0102934 A1 | 5/2004 | Chang |
| 2004/0107412 A1 | 6/2004 | Pack et al. |
| 2004/0119036 A1 | 6/2004 | Ye et al. |
| 2004/0120569 A1 | 6/2004 | Hung et al. |
| 2004/0133369 A1 | 7/2004 | Pack et al. |
| 2004/0174506 A1 | 9/2004 | Smith |
| 2004/0223639 A1 | 11/2004 | Sato et al. |
| 2004/0228515 A1 | 11/2004 | Okabe et al. |
| 2004/0234120 A1 | 11/2004 | Honda et al. |
| 2004/0243320 A1 | 12/2004 | Chang et al. |
| 2004/0254752 A1 | 12/2004 | Wisniewski et al. |
| 2005/0004774 A1 | 1/2005 | Volk et al. |
| 2005/0008218 A1 | 1/2005 | O'Dell et al. |
| 2005/0010890 A1 | 1/2005 | Nehmadi et al. |
| 2005/0062962 A1 | 3/2005 | Fairley |
| 2005/0117796 A1 | 6/2005 | Matsui et al. |
| 2005/0132306 A1 | 6/2005 | Smith |
| 2005/0141764 A1 | 6/2005 | Tohyama et al. |
| 2005/0166174 A1 | 7/2005 | Ye et al. |
| 2005/0184252 A1 | 8/2005 | Ogawa et al. |
| 2005/0190957 A1 | 9/2005 | Cai et al. |
| 2005/0198602 A1 | 9/2005 | Brankner |
| 2006/0000964 A1 | 1/2006 | Ye et al. |
| 2006/0036979 A1 * | 2/2006 | Zurbrick et al. ............... 716/4 |
| 2006/0048089 A1 | 3/2006 | Schwarzbaned |
| 2006/0051682 A1 | 3/2006 | Hess et al. |
| 2006/0062445 A1 | 3/2006 | Verma et al. |
| 2006/0082763 A1 | 4/2006 | The et al. |
| 2006/0159333 A1 | 7/2006 | Ishikawa |
| 2006/0161452 A1 | 7/2006 | Hess et al. |
| 2006/0193506 A1 | 8/2006 | Dorphan et al. |
| 2006/0193507 A1 | 8/2006 | Sali et al. |
| 2006/0236294 A1 | 10/2006 | Saidin |
| 2006/0236297 A1 | 10/2006 | Melvin et al. |
| 2006/0239536 A1 | 10/2006 | Shibuya et al. |
| 2006/0265145 A1 | 11/2006 | Huet et al. |
| 2006/0266243 A1 | 11/2006 | Percin et al. |
| 2006/0269120 A1 | 11/2006 | Nehmadi et al. |
| 2006/0273242 A1 | 12/2006 | Hunsche et al. |
| 2006/0273266 A1 | 12/2006 | Preil et al. |
| 2006/0291714 A1 | 12/2006 | Wu et al. |
| 2006/0292463 A1 | 12/2006 | Best et al. |
| 2007/0002322 A1 | 1/2007 | Borodovsky et al. |
| 2007/0019171 A1 | 1/2007 | Smith |
| 2007/0031745 A1 | 2/2007 | Ye et al. |
| 2007/0032896 A1 | 2/2007 | Ye et al. |
| 2007/0035322 A1 | 2/2007 | Kang |
| 2007/0035712 A1 | 2/2007 | Gassner et al. |

| | | | |
|---|---|---|---|
| 2007/0035728 | A1 | 2/2007 | Kekare et al. |
| 2007/0052963 | A1 | 3/2007 | Orbon |
| 2007/0064995 | A1 | 3/2007 | Oaki et al. |
| 2007/0133860 | A1 | 6/2007 | Lin |
| 2007/0156379 | A1 | 7/2007 | Kulkarni et al. |
| 2007/0230770 | A1* | 10/2007 | Kulkarni et al. .............. 382/149 |
| 2007/0248257 | A1 | 10/2007 | Bruce et al. |
| 2007/0280527 | A1 | 12/2007 | Almogy et al. |
| 2007/0288219 | A1 | 12/2007 | Zafar et al. |
| 2008/0013083 | A1 | 1/2008 | Kirk et al. |
| 2008/0049994 | A1 | 2/2008 | Rognin et al. |
| 2008/0072207 | A1 | 3/2008 | Verma et al. |
| 2008/0081385 | A1* | 4/2008 | Marella et al. .................. 438/14 |
| 2008/0163140 | A1 | 7/2008 | Fouquet et al. |
| 2008/0167829 | A1 | 7/2008 | Park et al. |
| 2008/0250384 | A1 | 10/2008 | Duffy et al. |
| 2008/0295047 | A1 | 11/2008 | Nehmadi et al. |
| 2008/0304056 | A1 | 12/2008 | Alles et al. |
| 2009/0016595 | A1 | 1/2009 | Peterson et al. |
| 2009/0024967 | A1 | 1/2009 | Su et al. |
| 2009/0037134 | A1 | 2/2009 | Kulkarni et al. |
| 2009/0041332 | A1 | 2/2009 | Bhaskar et al. |
| 2009/0043527 | A1 | 2/2009 | Park et al. |
| 2009/0055783 | A1 | 2/2009 | Florence et al. |
| 2009/0080759 | A1 | 3/2009 | Bhaskar et al. |
| 2009/0210183 | A1 | 8/2009 | Rajski et al. |

FOREIGN PATENT DOCUMENTS

| | | |
|---|---|---|
| EP | 0370322 | 5/1990 |
| EP | 1061358 | 12/2000 |
| EP | 1061571 | 12/2000 |
| EP | 1065567 | 1/2001 |
| EP | 1066925 | 1/2001 |
| EP | 1069609 | 1/2001 |
| EP | 1093017 | 4/2001 |
| EP | 1480034 | 11/2004 |
| EP | 1696270 | 8/2006 |
| JP | 2002-071575 | 3/2002 |
| JP | 2002-365235 | 12/2002 |
| JP | 2004-045066 | 2/2004 |
| KR | 10-2001-0037026 | 5/2001 |
| KR | 10-2001-0101697 | 11/2001 |
| KR | 1020030055848 | 7/2003 |
| KR | 10-2005-0092053 | 9/2005 |
| KR | 10-2006-0075691 | 7/2006 |
| WO | WO 98/57358 | 12/1998 |
| WO | WO 99/22310 | 5/1999 |
| WO | WO 99/25004 | 5/1999 |
| WO | WO 99/38002 | 7/1999 |
| WO | WO 99/41434 | 8/1999 |
| WO | WO 99/59200 | 11/1999 |
| WO | WO 00/03234 | 1/2000 |
| WO | WO 00/36525 | 6/2000 |
| WO | WO 00/55799 | 9/2000 |
| WO | WO 00/68884 | 11/2000 |
| WO | WO 00/70332 | 11/2000 |
| WO | WO 01/09566 | 2/2001 |
| WO | WO 01/40145 | 6/2001 |
| WO | WO 03/104921 | 12/2003 |
| WO | WO 2004/027684 | 4/2004 |
| WO | WO 2006/063268 | 6/2006 |
| WO | 2010/093733 | 8/2010 |

OTHER PUBLICATIONS

Barty et al., "Aerial Image Microscopes for the inspection of defects in EUV masks," Proceedings of SPIE, vol. 4889, 2002, pp. 1073-1084.
Budd et al., "A New Mask Evaluation Tool, the Microlithography Simulation Microscope Aerial Image Measurement System," SPIE vol. 2197, 1994, pp. 530-540.
Cai et al., "Enhanced Dispositioning of Reticle Defects Using the Virtual Stepper With Automoated Defect Severity Scoring," Proceedings of the SPIE, vol. 4409, Jan. 2001, pp. 467-478.
Comizzoli, "Uses of Corono Discharges in the Semiconfuctor Industry," J. Electrochem. Soc., 1987, pp. 424-429.
Contactless Electrical Equivalent Oxide Thickness Measurement, IBM Technical Disclosure Bulletin, vol. 29, No. 10, 1987, pp. 4622-4623.
Contactless Photovoltage vs. Bias Method for Determining Flat-Band Voltage, IBM Technical Disclosure Bulletin, vol. 32, vol. 9A, 1990, pp. 14-17.
Cosway et al., "Manufacturing Implementation of Corona Oxide Silicon (COS) Systems for Diffusion Furnace Contamination Monitoring," 1997 IEEE/SEMI Advanced Semiconductor Manufacturing Conference, pp. 98-102.
Diebold et al., "Characterization and produiction metrology of thin transistor gate oxide films," Materials Science in Semiconductor Processing 2, 1999, pp. 103-147.
Dirksen et al., "Impact of high order aberrations on the performance of the aberration monitor," Proc. of SPIE vol. 4000, Mar. 2000, pp. 9-17.
Dirksen et al., "Novel aberration monitor for optical lithography," Proc. of SPIE vol. 3679, Jul. 1999, pp. 77-86.
Garcia et al., "New Die to Database Inspection Algorithm for Inspection of 90-nm Node Reticles," Proceedings of SPIE, vol. 5130, 2003, pp. 364-374.
Granik et al., "Sub-resolution process windows and yield estimation technique based on detailed full-chip CD simulation," Mentor Graphics, Sep. 2000, 5 pages.
Hess et al., "A Novel Approach: High Resolution Inspection with Wafer Plane Defect Detection," Proceedings of SPIE—International Society for Optical Engineering; Photomask and Next-Generation Lithography Mask Technology 2008, vol. 7028, 2008.
Huang et al., "Process Window Impact of Progressive Mask Defects, Its Inspection and Disposition Techniques (go/no-go criteria) Via a Lithographic Detector," Proceedings of SPIE—The International Society for Optical Engineering; 25th Annual Bacus Symposium on Photomask Technology 2005, vol. 5992.
Hung et al., Metrology Study of Sub 20 Angstrom oxynitride by Corona-Oxide-Silicon (COS) and Conventional C-V Approaches, 2002, Mat. Res. Soc. Symp. Proc., vol. 716, pp. 119-124.
International Search Report for PCT/US2003/21907 mailed Jun. 7, 2004.
International Search Report for PCT/US2004/040733 mailed Dec. 23, 2005.
International Search Report and Written Opinion for PCT Appln. No. PCT/US08/050397 dated Jul. 11, 2008.
International Search Report and Written Opinion for PCT Appln. No. PCT/US06/61113 dated Jul. 16, 2008.
International Search Report and Written Opinion for PCT/US2008/062873 mailed Aug. 12, 2008.
International Search Report and Written Opinion for PCT Appln. No. PCT/US2008/063008 dated Aug. 18, 2008.
International Search Report for PCT/US2008/62875 mailed Sep. 10, 2008.
International Search Report and Written Opinion for PCT Appln. No. PCT/US06/61112 dated Sep. 25, 2008.
International Search Report for PCT/US2008/70647 mailed Dec. 16, 2008.
International Search Report and Written Opinion for PCT/US2008/073706 mailed Jan. 29, 2009.
International Search Report and Written Opinion for PCT/US2008/072636 mailed Jan. 29, 2009.
Karklin et al., "Automatic Defect Severity Scoring for 193 nm Reticle Defect Inspection," Proceedings of SPIE—The International Society for Optical Engineering, 2001, vol. 4346, No. 2, pp. 898-906.
Lo et al., "Identifying Process Window Marginalities of Reticle Designs for 0.15/0.13 µm Technologies," Proceedings of SPIE vol. 5130, 2003, pp. 829-837.
Lorusso et al. "Advanced DFM Applns. Using design-based metrology on CDSEM," SPIE vol. 6152, Mar. 27, 2006.
Lu et al., "Application of Simulation Based Defect Printability Analysis for Mask Qualification Control," Proceedings of SPIE, vol. 5038, 2003, pp. 33-40.
Mack, "Lithographic Simulation: A Review," Proceedings of SPIE vol. 4440, 2001, pp. 59-72.
Martino et al., "Application of the Aerial Image Measurement System (AIMS(TM)) to the Analysis of Binary Mask Imaging and Resolution Enhancement Techniques," SPIE vol. 2197, 1994, pp. 573-584.
Miller, "A New Approach for Measuring Oxide Thickness," Semiconductor International, Jul. 1995, pp. 147-148.

Nagpal et al., "Wafer Plane Inspection for Advanced Reticle Defects," Proceedings of SPIE—The International Society for Optical Engineering; Photomask and Next-Generation Lithography Mask Technology. vol. 7028, 2008.

Numerical Recipes in C. The Art of Scientific Computing, 2nd Ed., © Cambridge University Press 1988, 1992, p. 683.

Otsu, "A Threshold Selection Method from Gray-Level Histograms," IEEE Transactions on Systems, Man, and Cybernetics, vol. SMC-9, No. 1, Jan. 1979, pp. 62-66.

Pang et al., "Simulation-based Defect Printability Analysis on Alternating Phase Shifting Masks for 193 nm Lithography," Proceedings of SPIE, vol. 4889, 2002, pp. 947-954.

Pettibone et al., "Wafer Printability Simulation Accuracy Based on UV Optical Inspection Images of Reticle Defects," Proceedings of SPIE—The Intenational Society for Optical Engineering 1999 Society of Photo-Optical Instrumentation Engineers, vol. 3677, No. II, 1999, pp. 711-720.

Phan et al., "Comparison of Binary Mask Defect Printability Analysis Using Virtual Stepper System and Aerial Image Microscope System," Proceedings of SPIE—The International Society for Optical Engineering 1999 Society of Photo-Optical Instrumentation Engineers, vol. 3873, 1999, pp. 681-692.

Sahouria et al., "Full-chip Process Simulation for Silicon DRC," Mentor Graphics, Mar. 2000, 6 pages.

Schroder et al., Corono-Oxide-Semiconductor Device Characterization, 1998, Solid-State Electronics, vol. 42, No. 4, pp. 505-512.

Schroder, "Surface voltage and surface photovoltage: history, theory and applications," Measurement Science and Technology, vol. 12, 2001, pp. R16-R31.

Schroder, Contactless Surface Charge Semiconductor Characterization, Apr. 2002, Materials Science and Engineering B, vol. 91-92, pp. 196-228.

Schurz et al., "Simulation Study of Reticle Enhancement Technology Applications for 157 nm Lithography," SPIE vol. 4562, 2002, pp. 902-913.

Svidenko et al. "Dynamic Defect-Limited Yield Prediction by Criticality Factor," ISSM Paper: YE-O-157, 2007.

U.S. Appl. No. 10/677,445 (Horner et al.) entitled Methods for Non-Contacting Differential Voltage Measurements filed Oct. 2, 2003.

U.S. Appl. No. 10/778,752 (Mack et al.) entitled Methods for Improved Monitor and Control of Lithography Processes filed Feb. 13, 2004.

U.S. Appl. No. 11/154,310 (Verma et al.) entitled Computer-Implemented Methods, Simulation Engines and Systems for filed Jun. 16, 2005.

U.S. Appl. No. 12/102,343 (Chen et al.) entitled Methods and Systems for Determining a Defect Criticality Index for Defects on Wafers filed Apr. 14, 2008.

U.S. Appl. No. 60/418,887 (Su et al.) entitled Methods and Systems for Inspecting Reticles Using Aerial Imaging and Die-To-Database Detection filed Oct. 15, 2002.

U.S. Appl. No. 60/418,994 (Stokowski et al.) entitled Methods and Systems for Reticle Inspection and Defect Review Using Aerial Imaging filed Oct. 15, 2002.

U.S. Appl. No. 60/419,028 (Stokowski et al.) entitled Methods and Systems for Inspecting Reticles Using Aerial Imaging at Off-Stepper Wavelengths filed Oct. 15, 2002.

U.S. Appl. No. 60/451,707 (Howard et al.) entitled Methods and Systems for Classifying and Analyzing Defects on Reticles filed Mar. 4, 2003.

U.S. Appl. No. 60/526,881 (Hess et al.) entitled Designer Intent filed Dec. 4, 2003.

U.S. Appl. No. 60/609,670 (Preil et al.) entitled Methods, Systems, and Carrier Media for Evaluating Reticle Layout Data filed Sep. 14, 2004.

U.S. Appl. No. 60/681,095 (Nehmadi et al.) entitled Methods in Mask and Process Qualification filed May 13, 2005.

U.S. Appl. No. 60/684,360 (Nehmadi et al.) entitled Design-Based Inspection filed May 24, 2005.

U.S. Appl. No. 60/738,290 (Kulkarni et al.) entitled Methods and Systems for Utilizing Design Data in Combination With Inspection Data filed Nov. 18, 2005.

U.S. Appl. No. 60/772,418 (Kirk et al.) entitled Methods and Systems for Determining a Characteristic of a Wafer filed Feb. 9, 2006.

Verkuil et al., "A Contactless Alternative to MOS Charge Measurements by Means of a Corona-Oxide-Semiconductor (COS) Technique,"Electrochem. Soc. Extended Abstracts, 1988, vol. 88-1, No. 169, pp. 261-262.

Verkuil, "Rapid Contactless Method for Measuring Fixed Oxide Charge ASsociated with Silicon Processing," IBM Technical Disclousre Bulletin, vol. 24, No. 6, 1981, pp. 3048-3053.

Volk et al. "Investigation of Reticle Defect Formation at DUV Lithography," 2002, BACUS Symposium on Photomask Technology.

Volk et al. "Investigation of Reticle Defect Formation at DUV Lithography," 2003, IEEE/SEMI Advanced Manufacturing Conference, pp. 29-35.

Volk at al., "Investigation of Smart Inspection of Critical Layer Reticles using Additional Designer Data to Determine Defect Significance," Proceeings of SPIE vol. 5256, 2003, pp. 489-499.

Weinberg, "Tunneling of Electrons from Si into Thermally Grown Si02," Solid-State Electronics, 1977, vol. 20, pp. 11-18.

Weinzierl et al., "Non-Contact Corona-Based Process Control Measurements: Where We've Been, Where We're Headed," Electrochemical Society Proceedings, Oct. 1999, vol. 99-16, pp. 342-350.

Yan et al., "Printability of Pellicle Defects in DUV 0.5 um Lithography," SPIE vol. 1604, 1991, pp. 106-117.

International Search Report & Written Opinion, PCT/US2008/066328, mailed Oct. 1, 2009.

O'Gorman et al., "Subpixel Registration Using a Concentric Ring Fiducial," Proceedings of the International Conference on Pattern Recognition, vol. ii, Jun. 16, 1990, pp. 249-253

Huang et al., "Using Design Based Binning to Improve Defect Excursion Control for 45nm Production," IEEE, International Symposium on Semiconductor Manufacturing, Oct. 2007, pp. 1-3.

Sato et al., "Defect Criticality Index (DCI): A new methodology to significantly improve DOI sampling rate in a 45nm production environment," Metrology, Inspection, and Process Control for Microlithography XXII, Proc. of SPIE vol. 6922, 692213 (2008), pp. 1-9.

Tang et al., "Analyzing Volume Diagnosis Results with Statistical Learning for Yield Improvement" 12th IEEE European Test Symposium, Freiburg 2007, IEEE European, May 20-24, 2007, pp. 145-150.

\* cited by examiner

METHODS AND SYSTEMS FOR CLASSIFYING DEFECTS DETECTED ON A RETICLE

BACKGROUND OF THE INVENTION

1. Field of the Invention

The present invention generally relates to methods and systems for classifying defects detected on a reticle. Certain embodiments relate to a method for assigning a classification to a defect detected on a reticle based on an impact that the defect will have on the performance of a device being fabricated on a wafer.

2. Description of the Related Art

The following description and examples are not admitted to be prior art by virtue of their inclusion in this section.

Fabricating semiconductor devices such as logic and memory devices typically includes processing a substrate such as a semiconductor wafer using a large number of semiconductor fabrication processes to form various features and multiple levels of the semiconductor devices. For example, lithography is a semiconductor fabrication process that involves transferring a pattern from a reticle to a resist arranged on a semiconductor wafer. Additional examples of semiconductor fabrication processes include, but are not limited to, chemical-mechanical polishing, etch, deposition, and ion implantation. Multiple semiconductor devices may be fabricated in an arrangement on a single semiconductor wafer and then separated into individual semiconductor devices.

The terms "reticle" and "mask" are used interchangeably herein. A reticle generally includes a transparent substrate such as glass, borosilicate glass, and fused silica having patterned regions of opaque material formed thereon. The opaque regions may be replaced by regions etched into the transparent substrate. Many different types of reticles are known in the art, and the term reticle as used herein is intended to encompass all types of reticles.

The layout of a reticle generally includes a plurality of polygons that define features in a pattern on the reticle. The polygons can be generally defined by their size and placement on the reticle. Each reticle is used to fabricate one of the various layers of the device being fabricated on the wafer. The layers of a device such as an integrated circuit (IC) may include, for example, a junction pattern in a semiconductor substrate, a gate dielectric pattern, a gate electrode pattern, a contact pattern in an interlevel dielectric, and an interconnect pattern on a metallization layer.

In particular, the reticle is used to pattern a resist in a lithography process step, and then the patterned resist is used to form features of devices on the wafer. Therefore, the patterned features that are formed on a reticle and are to be transferred to the wafer reflect the characteristics of the features that are included in the device design. In other words, the features that are formed on the reticle are based on and used to form individual components of the device. The complexity of the device design, therefore, has a direct impact on the manufacture and inspection of reticles. In particular, as the complexity of device designs increases, successful reticle manufacture becomes more difficult. For instance, as the dimensions of the device features and the spacings between the features decrease, the dimensions and spacings of features on the reticle also decrease. In this manner, it becomes more difficult to form these features on a reticle due to, for example, limitations of the reticle manufacturing process. In addition, as is known in the art, the difficulty of successfully reproducing these features on wafers increases as the dimensions and spacings decrease.

Due to the important role that reticles play in semiconductor fabrication, ensuring that the reticles have been manufactured satisfactorily (such that the reticles can be used to produce the desired images on wafers) is critical to successful semiconductor fabrication. For example, defects in reticles are a source of yield reduction in device manufacturing. Therefore, inspection of a reticle is a critical step in reticle manufacturing processes. In general, during a reticle inspection process, an image of the reticle is typically compared to a baseline image. The baseline image is either generated from the circuit pattern data or from an adjacent die on the reticle itself. Either way, the image features are analyzed and compared with corresponding features of the baseline image. Each feature difference may then be compared against a threshold value. If the image feature varies from the baseline feature by more than the predetermined threshold, a defect may be defined. Once a reticle is fabricated and inspected, it may be qualified as acceptable for manufacturing and released to manufacturing.

Although conventional reticle inspections provide adequate levels of detection accuracy for some applications, other applications require a higher sensitivity or lower threshold value (for identifying defects) while other applications require less stringent, higher threshold levels. Accordingly, some inspection methods have been developed that inspect reticles with varying stringency based on the intent of the device designer. Examples of such methods are illustrated in commonly owned U.S. Pat. No. 6,529,621 to Glasser et al. and U.S. Pat. No. 6,748,103 to Glasser et al., which are incorporated by reference as if fully set forth herein. In this manner, decisions as to the appropriate stringency that should be used to detect defects on reticles can be made based on the electrical significance of features in the reticle layout data.

Such methods have substantially improved the accuracy, meaningfulness, usefulness, and throughput of reticle inspection. However, such methods do not take into account a number of other variables that can be used to further increase the value of reticle inspection. For example, there are potentially many defects on a reticle that have little bearing on the performance or yield of the chip. These defects consume resources in the form of operator review time involved in determining the importance of a defect and potentially in reticle repair time or effective yield (i.e., post-repair yield) of the reticle manufacturing process. If the defect does not have a real impact on the chip yield or the chip performance, then those resources are not being efficiently deployed. Furthermore, if a reticle defect is unrepairable and yet will print on an active area of the wafer, then the reticle is currently discarded. If it can be determined that the defect does not have a performance impact on the chip, then the reticle could be used thereby saving both time and money. However, historically, reticle inspection has not considered final circuit performance on either the inspection sensitivity or defect classification.

Accordingly, it would be advantageous to develop methods and systems for classifying defects detected on a reticle based on the impact that the defects will have on the performance of a device being fabricated on a wafer thereby increasing the efficiency of reticle defect review and repair, increasing the effective yield of the reticle manufacturing process, and decreasing the cost and time associated with reticle manufacturing.

SUMMARY OF THE INVENTION

The following description of various embodiments of methods and systems is not to be construed in any way as limiting the subject matter of the appended claims.

One embodiment relates to a method for classifying defects detected on a reticle. The method includes determining an impact that a defect detected on a reticle will have on the performance of a device being fabricated on a wafer based on how at least a portion of the reticle prints or will print on the wafer. The defect is located in the portion of the reticle. The method also includes assigning a classification to the defect based on the impact.

In one embodiment, the method includes generating a simulated image that illustrates how at least the portion of the reticle will print on the wafer using an image of at least the portion of the reticle. The image is generated by inspection of the reticle. In one such embodiment, determining the impact includes determining the impact based on the simulated image. In another embodiment, the method includes generating an aerial image that illustrates how at least the portion of the reticle will print on the wafer. The aerial image is generated by inspection of the reticle. In one such embodiment, determining the impact includes determining the impact based on the aerial image. In an additional embodiment, the method includes generating an image of at least a portion of the wafer in which at least the portion of the reticle is printed. The image is generated by inspection of the wafer. In one such embodiment, determining the impact includes determining the impact based on the image.

In one embodiment, determining the impact includes simulating the impact that the defect will have on the performance of the device. In another embodiment, the performance of the device includes one or more electrical characteristics of the device, one or more thermal characteristics of the device, or some combination thereof.

In one embodiment, determining the impact is performed online during inspection of the reticle. In another embodiment, the method includes determining if the defect is to be reported in inspection results for the reticle based on the classification assigned to the defect.

In one embodiment, determining the impact is performed offline after inspection of the reticle. In another embodiment, determining the impact includes determining the impact based on how at least the portion of the reticle prints or will print on the wafer and based on how at least another portion of the reticle prints or will print on the wafer. In one such embodiment, another defect is located in the other portion. In an additional embodiment, determining the impact includes determining the impact based on how at least the portion of the reticle prints or will print on the wafer and based on how at least a portion of an additional reticle prints or will print on the wafer. The reticle and the additional reticle are printed or will be printed on different layers of the wafer.

In one embodiment, the performance of the device includes the performance of only a portion of the device. In another embodiment, the performance of the device includes the performance of the entire device.

In one embodiment, the method includes determining if the defect should be reviewed based on the classification and not based on information about the portion of the reticle in which the defect is located. In another embodiment, the method includes determining if the defect should be repaired based on the classification and not based on information about the portion of the reticle in which the defect is located. In an additional embodiment, the method includes determining if the reticle should be discarded based on the classification and not based on information about the portion of the reticle in which the defect is located.

In one embodiment, determining the impact and assigning the classification are performed for all defects detected on the reticle. In another embodiment, the method includes determining if defects detected on the reticle print or will print on the wafer based on how at least portions of the reticle corresponding to locations of the defects print or will print on the wafer. In one such embodiment, determining the impact and assigning the classification are performed for only defects that print or will print on the wafer.

Each of the steps of each of the embodiments of the method described above may be further performed as described herein. In addition, each of the embodiments of the method described above may include any other step(s) of any other method(s) described herein. Furthermore, each of the embodiments of the method described above may be performed by any of the systems described herein.

Another embodiment relates to a system configured to classify defects detected on a reticle. The system includes an inspection subsystem configured to detect a defect on a reticle and to acquire an image of at least a portion of the reticle in which the defect is located. The system also includes a computer subsystem that is configured to generate a simulated image that illustrates how at least the portion of the reticle will print on a wafer using the image. The computer subsystem is also configured to determine an impact that the defect will have on the performance of a device being fabricated on the wafer based on the simulated image. In addition, the computer subsystem is configured to assign a classification to the defect based on the impact. The system may be further configured as described herein.

An additional embodiment relates to another system configured to classify defects detected on a reticle. The system includes an inspection subsystem configured to acquire an image that illustrates how at least a portion of a reticle prints or will print on a wafer. A defect detected on the reticle is located in the portion of the reticle. The system also includes a computer subsystem configured to determine an impact that the defect will have on the performance of a device being fabricated on the wafer based on the image and to assign a classification to the defect based on the impact. The system may be further configured as described herein.

BRIEF DESCRIPTION OF THE DRAWINGS

Further advantages of the present invention may become apparent to those skilled in the art with the benefit of the following detailed description of the preferred embodiments and upon reference to the accompanying drawings in which.

Figure 1:
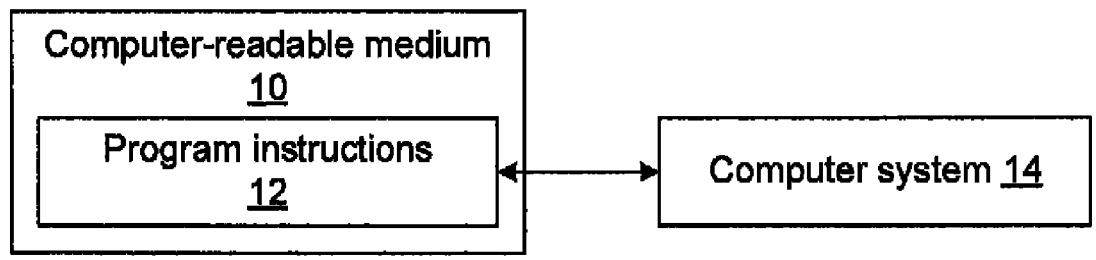
FIG. 1 is a block diagram illustrating one embodiment of a computer-readable medium that includes program instructions executable on a computer system for performing a method for classifying defects detected on a reticle.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

As used herein, the term "wafer" generally refers to a substrate formed of a semiconductor or non-semiconductor material. Examples of such a semiconductor or non-semiconductor material include, but are not limited to, monocrystalline silicon, gallium arsenide, and indium phosphide. Such substrates may be commonly found and/or processed in semiconductor fabrication facilities.

One or more layers may be formed upon a wafer. Many different types of such layers are known in the art, and the term wafer as used herein is intended to encompass a wafer on which all types of such layers may be formed. One or more layers formed on a wafer may be patterned. For example, a wafer may include a plurality of dies, each having repeatable patterned features. Formation and processing of such layers of material may ultimately result in completed semiconductor devices. As such, a wafer may include a substrate on which not all layers of a complete semiconductor device have been formed or a substrate on which all layers of a complete semiconductor device have been formed.

The term "device" as used herein may be generally defined as any device that can be fabricated on a wafer such as an integrated circuit (IC), a thin-film head die, a micro-electromechanical system (MEMS) device, flat panel displays, magnetic heads, magnetic and optical storage media, other components that may include photonics and optoelectronic devices such as lasers, waveguides and other passive components processed on wafers, print heads, and bio-chip devices processed on wafers.

One embodiment relates to a method for classifying defects detected on a reticle. The method includes determining an impact that a defect detected on a reticle will have on the performance of a device being fabricated on a wafer based on how at least a portion of the reticle prints or will print on the wafer. The defect is located in the portion of the reticle. The defect and other defects may be detected on the reticle as described further herein. In addition, the method may or may not include detecting the defects on the reticle. For example, the method may include detecting defects on the reticle as described further herein. Alternatively, inspection results for the reticle that include information about defects detected on the reticle may be acquired from another method and/or system that inspected the reticle or from a storage medium in which the inspection results have been stored (e.g., a storage medium coupled to a reticle inspection system, a storage medium in which the reticle inspection system stored the inspection results, etc.). As such, the method may include acquiring information about the defects detected on the reticle and using the information to perform the step(s) of the method described herein.

Determining the impact that the defect will have on the performance of the device may be performed according to any of the embodiments described herein. How at least the portion of the reticle in which the defect is located prints or will print on the wafer may be determined as described herein. In addition, the method may include determining how at least the portion of the reticle in which the defect is located prints or will print on the wafer as described herein. However, the method may not include determining how at least the portion of the reticle in which the defect is located prints or will print on the wafer. For example, information about how at least the portion of the reticle prints or will print on the wafer may be acquired from a method and/or system that determines and/or generates such information or from a storage medium in which such information has been stored by such a method and/or system. In this manner, the embodiments described herein may provide an understanding of the impact of the defect on the printed wafer as well as an understanding of that pattern change on the performance of the device (e.g., chip).

At least the portion of the reticle, printing or expected printing of which on a wafer on which determining the impact of the defect on the performance of the device is based, may vary depending on the defects and the features of the reticle that are or may be affected by the defect (i.e., features of the reticle whose fabrication on the reticle is affected by the defect and/or whose printing on the wafer is or may be affected by the defect). For example, at least the portion of the reticle may include only the defect and the features of the reticle that are or may be affected by the defect. Alternatively, at least the portion of the reticle may include the defect, features of the reticle that are or may be affected by the defect, and some portion of the reticle surrounding the defect and the features. In another alternative, at least the portion of the reticle may include the entire reticle.

In one embodiment, the method includes generating a simulated image that illustrates how at least the portion of the reticle will print on the wafer using an image of at least the portion of the reticle. The image is generated by inspection of the reticle. The method may or may not include performing an inspection of the reticle to detect the defects on the reticle as described above. The inspection of the reticle may be a substantially high resolution inspection. For example, the reticle may be inspected using a reticle inspection system capable of inspecting a reticle with substantially high resolution such as the TeraScan and TeraScanHR systems that are commercially available from KLA-Tencor, San Jose, Calif. Therefore, the image of at least the portion of the reticle generated by inspection of the reticle may be a substantially high resolution image of at least the portion of the reticle. The method may include performing computer simulation to generate the pattern on the wafer using the image. For example, the wafer plane inspection (WPI) mode, which is commercially available from KLA-Tencor, may form the starting point for the embodiments described herein. WPI takes measured images of a reticle, including the defects, and performs a lithography simulation that generates detailed patterns that would result on a wafer from the use of the reticle. In this manner, the method may use a substantially high resolution inspection of a reticle and lithographic simulations.

In one such embodiment, determining the impact includes determining the impact based on the simulated image. For example, the patterns generated by lithography simulation can be used in downstream simulations of the performance of the device (e.g., circuit). In this manner, one may start with an inspection that generates wafer patterns which are then used to drive device (e.g., chip) performance simulations. Determining the impact based on the simulated image may be performed as described further herein.

In another embodiment, the method includes generating an aerial image that illustrates how at least the portion of the reticle will print on the wafer. The aerial image is generated by inspection of the reticle. The method may or may not include performing an inspection of the reticle to detect the defects on the reticle as described herein. The inspection of the reticle may be an aerial image inspection. For example, an aerial image inspection system can be used to generate the aerial image. The aerial image inspection may be performed as described herein, and the aerial image inspection system may be configured as described herein. In one such embodiment, determining the impact includes determining the impact based on the aerial image. In this manner, one can start with an inspection that generates wafer patterns which are then used to drive device (e.g., chip) performance simulations. Determining the impact based on the aerial image may be performed as described further herein.

In an additional embodiment, the method includes generating an image of at least a portion of the wafer in which at least the portion of the reticle is printed. The image is generated by inspection of the wafer. The method may or may not include inspecting the wafer. For example, the method may include performing an inspection to detect the defects on the reticle, and the inspection can be an inspection of a wafer used to determine reticle defects (e.g., as in image qualification applications). In one such embodiment, determining the impact includes determining the impact based on the image. For example, the method may be performed by using relatively detailed wafer inspection results to drive the performance simulation. The wafer inspection may be performed using local scanning electron microscope (SEM) images or atomic force microscope (AFM) images or a relatively large scale electron beam inspection of the wafer. Other approaches can be considered as long as they produce results that are accurate enough to drive the performance simulation. Determining the impact based on the image generated by inspection of the wafer may be performed as described further herein.

In one embodiment, determining the impact includes simulating the impact that the defect will have on the performance of the device. For example, determining the impact may include using appropriate simulations to determine the performance of the device (e.g., chip) based on how at least the portion of the reticle prints or will print on the wafer. The simulations may be performed using any suitable method, algorithm, software, hardware, or some combination thereof. For example, suitable software that may be used to simulate the performance of a device includes PrimeTime® static timing analysis software that is commercially available from Synopsys, Mountain View, Calif. and various software commercially available from Cadence Design Systems, San Jose, Calif., Mentor Graphics, Wilsonville, Oreg., and Blaze DFM, Sunnyvale, Calif. The simulated performance of the device will indicate the impact that the defect will have on the device.

The impact that the defect will have on the performance of the device can also be determined by comparing the simulated performance of the device to how the device was designed to perform. Information about how the device was designed to perform can be acquired from any suitable source (e.g., the design itself). In addition, or alternatively, the performance of the device may be simulated based on how at least the portion of the reticle would be printed on the wafer if the defect was not located in the portion of the reticle. For example, at least a portion of the reticle design data or layout may be used as input to one or more simulations that can be used to generate one or more images that illustrate how at least the portion of the reticle will print on the wafer. Those one or more simulated images can also be used as input to the simulations of the device performance, and the results of those simulations can then be compared to the simulations for at least the portion of the reticle in which the defect is located. In this manner, the change in the device performance due to the reticle defect can be determined thereby determining the impact that the defect will have on the device performance.

In some embodiments, the performance of the device includes one or more electrical characteristics of the device, one or more thermal characteristics of the device, or some combination thereof. For example, the performance of the device can include the timing of circuitry in the device, the leakage current, the power generation, the thermal characteristics, opens and/or shorts in the circuit, and the like, or some combination thereof.

In one embodiment, determining the impact is performed online during inspection of the reticle. For example, if a defect is detected on the reticle during inspection, the impact that the defect will have on the performance of the device may be determined while the reticle is being inspected for additional defects. In this manner, the simulation of the device (e.g., circuit) performance can be performed as an integrated (online) part of the inspection. If the simulation is integrated, the performance simulation may be performed on a computer included in and/or connected to the inspection system.

In another embodiment, determining the impact is performed offline after inspection of the reticle. For example, the simulation of the device (e.g., circuit) performance can be performed as an offline step. If the simulation is to be performed offline, then the defect images, or the wafer pattern, can be exported to an external computer where the calculation is performed.

In one embodiment, determining the impact includes determining the impact based on how at least the portion of the reticle prints or will print on the wafer and based on how at least another portion of the reticle prints or will print on the wafer. In one such embodiment, another defect is located in the other portion of the reticle. For example, if the performance impact calculations are performed offline, there can be the advantage of integrating results for multiple defects on a reticle to see how various defects "stack up." In one such example, there can be two or more defects on the same reticle that interact to push the performance of the device (e.g., chip) outside of the tolerance zone. As an example, there can be two or more gates within the critical timing circuit that might be acceptable by themselves, but when combined, violate the timing criteria for the device (e.g., chip). Determining the impact in this manner may be performed as described further herein.

In another embodiment, determining the impact includes determining the impact based on how at least the portion of the reticle prints or will print on the wafer and based on how at least a portion of an additional reticle prints or will print on the wafer. In one such embodiment, the reticle and the additional reticle are printed or will be printed on different layers of the wafer. For example, if the performance impact calculations are performed offline, there can be the advantage of integrating results from multiple reticles to see how various defects "stack up." In one such example, there can be two or more defects on different reticles that interact to push the performance of the device (e.g., chip) outside of the tolerance zone. As an example, there can be two or more elements within the critical timing circuit that might be acceptable by themselves, but when combined, violate the timing criteria for the device (e.g., chip).

In one embodiment, the performance of the device includes the performance of only a portion of the device. For example, the portion of the device may include only the portion of the device that the defect may impact the performance of. In one such example, the design of the reticle and/or device and the location of the defect within the reticle may be used to determine which elements of the device the defect may impact the performance of. Those elements may then be used to determine the portion of the device for which the impact of the defect on the performance will be determined. The impact that the defect will have on the performance of that portion of the device may then be determined as described herein. The impact that a defect will have on the performance of only a portion of the device can be determined relatively quickly.

Therefore, determining the impact that a defect will have on the performance of only a portion of the device may be particularly advantageous when determining the impact is performed online during inspection.

In another embodiment, the performance of the device includes the performance of the entire device. For example, with sufficient computer resources, the full performance analysis of the device (e.g., chip) can be performed using information about how the entire reticle prints or will print on the wafer (e.g., using a simulated image such as that described further herein). In this case, one does not just focus on the defects that were detected, but rather the entire device (e.g., chip). However, the performance of the entire device can be used to determine the impact of individual defects detected on the reticle and the reticle as a whole on the performance of the device. Of course, for performance analysis of the entire device, a knowledge of the interconnects and the performance of other wafer layers is an important aspect. Information about the interconnects and the performance of other wafer layers may be acquired from any suitable source. For example, such information can be acquired from an electronic design automation (EDA) tool and may have any suitable format such as a graphical data stream (GDS) file, any other standard machine-readable file, any other suitable file known in the art, and a design database. A GDSII file is one of a class of files used for the representation of design layout data. Other examples of such files include GL1 and OASIS files.

The method also includes assigning a classification to the defect based on the impact. In this manner, the method uses device (e.g., circuit) performance to classify a reticle defect. Therefore, the method includes classifying the reticle defect appropriately based on the impact of the defect on the reticle performance. Classifying reticle defects in this manner is advantageous because it is the impact of the printing defects on the performance of the device (e.g., chip) that is the key to the proper classification of the defects. Therefore, the embodiments described herein provide the ultimate use of the defect relevance for classification of the defects. As such, the embodiments described herein optimize the classification of defects on reticles used for semiconductor lithography based on the impact of the defect on final device (e.g., circuit) performance. The classifications that are assigned to the defects may include any classifications that can be used to indicate how the defects will impact the performance of the device and therefore may vary depending on the defects themselves as well as the impact that is determined. Examples of suitable classifications that may be assigned by the embodiments described herein include, but are certainly not limited to, "critical timing defect," "non-critical timing defect," "critical thermal excursion," "non-critical thermal excursion," "reduced clock speed defect," and the like.

In another embodiment, the method includes determining if the defect is to be reported in inspection results for the reticle based on the classification assigned to the defect. In this manner, the embodiments described herein can use device (e.g., circuit) performance as a guide to drive reticle inspection sensitivity. For example, the defects can be detected on the reticle with substantially high sensitivity. Although inspecting the reticle with substantially high sensitivity can result in a significant and sometimes overwhelming number of defects being detected on the reticle, a substantial portion of which may include nuisance, the embodiments described herein can essentially filter those detected defects based on the impact that the defects will have on the performance of the device. For example, if the simulation of the device (e.g., circuit) performance is performed online, a defect can either be directly ignored if it is determined to have insignificant performance impact (such that the defect is not reported or not included in results of the embodiments described herein) or the determined performance impact of the defect can result in an automatic classification of the defect that is still reported.

In any case, the selective reporting of defects or the classifications assigned to the defects can indicate those defects that will have an impact on the performance of the device. Therefore, the reticle inspection sensitivity can be made more sensitive to the performance impact of the defects on the device. As such, the results produced by the embodiments described herein will be highly relevant to the most important thing in semiconductor device manufacturing, namely the performance and yield of the manufacturing process. In this manner, the embodiments described herein have the advantage of focusing inspection resources only on those defects that have bottom-line performance impact on the device (e.g., chip). In addition, detecting defects on the reticle with substantially high sensitivity will essentially ensure that any and all defects that may have an impact on the performance of the device will be captured. Therefore, the embodiments described herein can be used to optimize the inspection of defects on reticles used for semiconductor lithography based on the impact of the defects on the final device (e.g., circuit) performance.

In one embodiment, the method includes determining if the defect should be reviewed based on the classification and not based on information about the portion of the reticle in which the defect is located. In this manner, the embodiments described herein have the advantage of focusing the inspection resources as well as review resources only on those defects that have bottom-line performance impact on the device (e.g., chip). In addition, unlike methods that select defects for review based on whether or not the defects are located in a particular (e.g., critical) portion of the reticle, the embodiments described herein may not select defects for review based on information (e.g., criticality) about the portions of the reticle in which the defects are located. Furthermore, other methods that select defects for review based on whether or not the defects are located in a particular portion of the reticle select the defects without regard to the impact that the defects will have on the performance of the device. Therefore, the embodiments described herein can select defects for review that are most relevant to the performance of the device and the yield of the manufacturing process because the defects are not selected based on information about the portions of the reticle in which the defects are located regardless of the impact that the defects will have on the performance of the device. Review of the defects that are selected may be performed in any suitable manner using any suitable defect review system. In addition, the embodiments described herein may or may not include reviewing the defects after they have been selected for review.

In another embodiment, the method includes determining if the defect should be repaired based on the classification and not based on information about the portion of the reticle in which the defect is located. In this manner, the embodiments described herein have the advantage of focusing the inspection resources as well as potential reticle repair resources only on those defects that have bottom-line performance impact on the device (e.g., chip). In addition, unlike methods that select defects for repair based on whether or not the defects are located in a particular (e.g., critical) portion of the reticle, the embodiments described herein may not select defects for repair based on information (e.g., criticality) about the portions of the reticle in which the defects are located. Furthermore, other methods that select defects for repair based on whether or not the defects are located in a particular portion of the reticle select the defects without regard to the impact that the defects will have on the performance of the device. Therefore, the embodiments described herein can select defects for repair that are most relevant to the performance of the device and the yield of the manufacturing process because the defects are not selected based on information about the portions of the reticle in which the defects are located regardless of the impact that the defects will have on the performance of the device. Repair of the defects that are selected may be performed in any suitable manner using any suitable defect repair system. In addition, the embodiments described herein may or may not include repairing the defects after they have been selected for repair.

In an additional embodiment, the method includes determining if the reticle should be discarded based on the classification and not based on information about the portion of the reticle in which the defect is located. For example, as reticle generation and lithography become increasingly difficult, there will be more unrepairable defects on a reticle. If a reticle must be discarded for unrepairable printing defects on active parts of the device (e.g., circuit), then yield of the reticle manufacturing process will suffer. The embodiments described herein would allow the continued use of a defective reticle where the defects that print on active circuit elements do not have a limiting performance impact on the device (e.g., chip). In this manner, unlike methods that determine whether the reticle should be discarded based on whether or not the defects are located in a particular (e.g., critical) portion of the reticle, the embodiments described herein may not determine if the reticle is to be discarded based on information (e.g., criticality) about the portion of the reticle in which the defects are located. In addition, other methods that determine if a reticle is to be discarded based on whether or not defects are located in a particular portion of the reticle determine whether the reticle should be discarded without regard to the impact that the defects will have on the performance of the device. Therefore, the embodiments described herein can determine if a reticle is to be discarded based on the defects that are most relevant to the performance of the device and the yield of the manufacturing process because whether or not the reticle is to be discarded is not based on information about the portion of the reticle in which the defects are located regardless of the impact that the defects will have on the performance of the device.

In one embodiment, determining the impact and assigning the classification are performed for all defects detected on the reticle. For example, the impact that a defect will have on the performance of the device may be determined regardless of information about the portion of the reticle in which the defect is located, regardless of information about the portion of the device in which the defect may print, regardless of whether or not the defect will print on the wafer or how the defect will print on the wafer, and regardless of any information (e.g., size) about the defect itself.

In another embodiment, the method includes determining if defects detected on the reticle print or will print on the wafer based on how at least portions of the reticle corresponding to locations of the defects print or will print on the wafer. In one such embodiment, determining the impact and assigning the classification are performed for only defects that print or will print on the wafer. In this manner, how the defects detected on the reticle print or will print on the wafer, which may be determined as described herein, may be used to identify candidate defects for the steps of the embodiments described herein. As such, the method may include using appropriate simulations to determine the impact of only printing defects on the reticle performance.

The embodiments described herein, therefore, have a number of advantages over other methods for adjusting the sensitivity of reticle inspection and classifying reticle defects. For example, steps have been taken to inspect reticles more efficiently. In one such example, "Smart Inspection" methods and systems such as those described in commonly owned U.S. patent application Ser. No. 10/883,372 filed Jul. 1, 2004 by Volk et al. published as U.S. Patent Application Publication No. 2005/0004774 on Jan. 6, 2005 and Ser. No. 11/003, 291 filed Dec. 3, 2004 by Hess et al. published as U.S. Patent Application Publication No. 2006/0051682 on Mar. 9, 2006, which are incorporated by reference as if fully set forth herein, and "Sensitivity Control Layer" (SCL) inspection modes such as those described in commonly owned U.S. Pat. No. 6,529,621 to Glasser et al. and U.S. Pat. No. 6,748,103 to Glasser et al., which are incorporated by reference as if fully set forth herein, have been developed in which user-generated control layers may direct the sensitivity of inspection and classification of defects in different regions of the plate. Methods and systems for using an SCL-type inspection mode for reticle design data are described in commonly owned U.S. patent application Ser. No. 11/003,291 filed Dec. 3, 2004 by Hess et al. published as U.S. Patent Application Publication No. 2006/0051682 on Mar. 9, 2006 and Ser. No. 11/048,630 filed Jan. 31, 2005 by Preil et al. published as U.S. Patent Application Publication No. 2006/0236294 on Oct. 19, 2006, which are incorporated by reference as if fully set forth herein. However, these approaches can have the disadvantage of requiring an external input to drive the sensitivity and classification rules. In addition, these methods and systems can use the significance of a region of the plate, but may not have any knowledge of the specific performance impact of any given defect.

Methods and systems for WPI mode such as those described above have also been developed. In general, those methods and systems use lithographic simulations to determine which reticle defects will have a printing impact on the wafer. Examples of such methods and systems are illustrated in commonly owned U.S. patent application Ser. No. 10/793, 599 filed Mar. 4, 2004 by Howard et al., which is incorporated by reference as if fully set forth herein. The degree to which a reticle defect prints on a wafer is certainly relevant, but printing defects can have no yield or performance impact. For example, not only can there be defects on dummy figures used to better enable chemical-mechanical polishing or to rivet different wafer layers together, but other defects on active elements may not have any impact on the timing, thermal characteristics, or other characteristics of the device or yield of the reticle. These defects do print, but they may be allowed to remain on the reticle as the resultant device (e.g., circuit) impact is acceptable.

In contrast, the embodiments described herein provide a potentially important design for manufacturing (DFM) application for reticle defects. In particular, the embodiments described herein reach to the core of DFM type applications in that they focus on final device (e.g., chip) performance. However, the embodiments described herein can be used with other method(s) described above (e.g., to effectively pre-screen reticle defects for the method step(s)). For example, the embodiments described herein can use the significance of a region of the reticle as described in the above-referenced patents to Glasser et al. to eliminate any defects that are in non-critical regions of the reticle from processing in steps described herein. In particular, if a reticle defect is located in a non-critical region of the reticle, the method may determine that how at least the portion of the reticle in which the defect is located will print on the wafer is not to be determined, the impact that the defect will have on the performance of the device is not to be determined, and the defect is not to be classified and/or reported. In another example, the methods and systems described in the above-referenced patent application by Howard et al. may be used to determine if the defects detected on the reticle will print on the wafer based on how at least portions of the reticle corresponding to locations of the defects will print on the wafer. Determining the impact and assigning the classification as described herein may then be performed for only those defects that will print on the wafer and possibly only those defects that will print on the wafer and are located in electrically active portions of the device.

The images and/or other data and/or results of any of the step(s) described herein may be stored using systems and methods such as those described in commonly owned U.S. patent application Ser. No. 12/234,201 by Bhaskar et al. filed Sep. 19, 2008, which is incorporated by reference as if fully set forth herein. The stored images and/or other data and/or results of any of the step(s) described herein may then be used in step(s) of the embodiments described herein. The embodiments described herein may include any step(s) of any method(s) described in this patent application.

The embodiments described herein may also include storing results of one or more steps of one or more methods described herein in a storage medium. The results may include any of the results described herein. The results may be stored in any manner known in the art. The storage medium may include any suitable storage medium known in the art. After the results have been stored, the results can be accessed in the storage medium and used by any of the method or system embodiments described herein, any other method, or any other system. Furthermore, the results may be stored "permanently," "semi-permanently," temporarily, or for some period of time. For example, the storage medium may be random access memory (RAM), and the results may not necessarily persist indefinitely in the storage medium.

Another embodiment relates to a computer-implemented method for classifying defects detected on a reticle. The computer-implemented method includes determining an impact that a defect detected on a reticle will have on the performance of a device being fabricated on a wafer based on how at least a portion of the reticle prints or will print on the wafer. The defect is located in the portion of the reticle. Determining the impact may be performed as described further herein. The performance of the device may include any performance of the device described herein. The computer-implemented method also includes assigning a classification to the defect based on the impact. Assigning the classification may be performed as described further herein. The classification may include any of the classifications described herein. The computer-implemented method may include any other step(s) of any other method(s) described herein.

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals.

An additional embodiment relates to a computer-readable medium that includes program instructions executable on a computer system for performing a computer-implemented method for classifying defects detected on a reticle. One such embodiment is shown in FIG. 1. For example, as shown in FIG. 1, computer-readable medium 10 includes program instructions 12 executable on computer system 14 for performing a computer-implemented method for classifying defects detected on a reticle. The computer-implemented method may include the computer-implemented method described above. In addition, the computer-implemented method may include any step(s) of any of the method embodiment(s) described herein.

Program instructions 12 implementing methods such as those described herein may be transmitted over or stored on computer-readable medium 10. The computer-readable medium may be a storage medium such as a read-only memory, a RAM, a magnetic or optical disk, a magnetic tape, or any other suitable computer-readable medium known in the art.

The program instructions may be implemented in any of various ways, including procedure-based techniques, component-based techniques, and/or object-oriented techniques, among others. For example, the program instructions may be implemented using Matlab, Visual Basic, ActiveX controls, C, C++ objects, C#, JavaBeans, Microsoft Foundation Classes ("MFC"), or other technologies or methodologies, as desired.

Computer system 14 may take various forms, including a personal computer system, mainframe computer system, workstation, system computer, image computer, programmable image computer, parallel processor, or any other device known in the art. In general, the term "computer system" may be broadly defined to encompass any device having one or more processors, which executes instructions from a memory medium.

Figure 2:
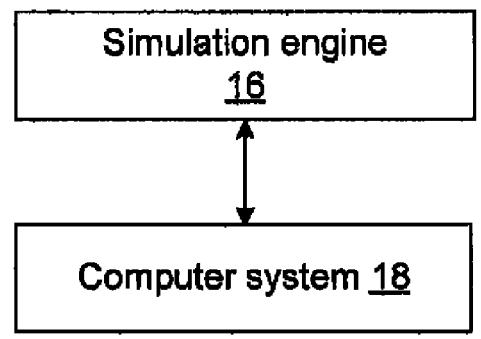
FIG. 2 is a block diagram illustrating one embodiment of a system configured to classify defects detected on a reticle.

FIG. 2 illustrates one embodiment of a system configured to classify defects detected on a reticle. The system includes simulation engine 16. Simulation engine 16 is configured to simulate the performance of a device being fabricated on a wafer based on how at least a portion of the reticle prints or will print on the wafer. A defect is located in the portion of the reticle. The simulation engine may be configured to simulate the performance of the device as described further herein. The simulation engine may include any suitable hardware and/or software including any of the hardware and/or software described herein that can be configured to perform the simulations described above. The performance of the device that is simulated by the simulation engine may include any device performance described herein.

The simulation engine may also be configured to perform any other simulations described herein. For example, the simulation engine may be configured to simulate how at least the portion of the reticle will print on the wafer. The simulation engine may be configured to simulate how at least the portion of the reticle will print on the wafer as described further herein. Alternatively, the system may include an additional simulation engine (not shown) that is configured to simulate how at least the portion of the reticle will print on the wafer. The additional simulation engine may include any suitable hardware and/or software including any of the hardware and/or software described herein that can be configured to perform the simulations described herein. Alternatively, the system may be configured to acquire one or more images that illustrate how at least the portion of the reticle prints or will print on the wafer (e.g., from a system, method, hardware, or software that generated the one or more images), and the simulation engine may be configured to use those one or more images to simulate the performance of the device as described further herein.

The system also includes computer system 18. Computer system 18 may be coupled to simulation engine 16 in any suitable manner. In addition, simulation engine 16 may be included in the computer system. The computer system is configured to determine an impact that the defect detected on the reticle will have on the performance of the device based on the performance of the device simulated by the simulation engine. The computer system may be configured to determine the impact according to any of the embodiments described herein. The computer system is also configured to assign a classification to the defect based on the impact. The computer system may be configured to assign the classification to the defect according to any of the embodiments described herein. The classification may include any of the classifications described herein. The computer system may also be configured to perform any other step(s) of any method(s) described herein. The computer system may include any suitable computer system that can be configured to perform the step(s) described above. The computer system may be further configured as described herein. In addition, the system shown in FIG. 2 may be further configured as described herein.

Figure 3:
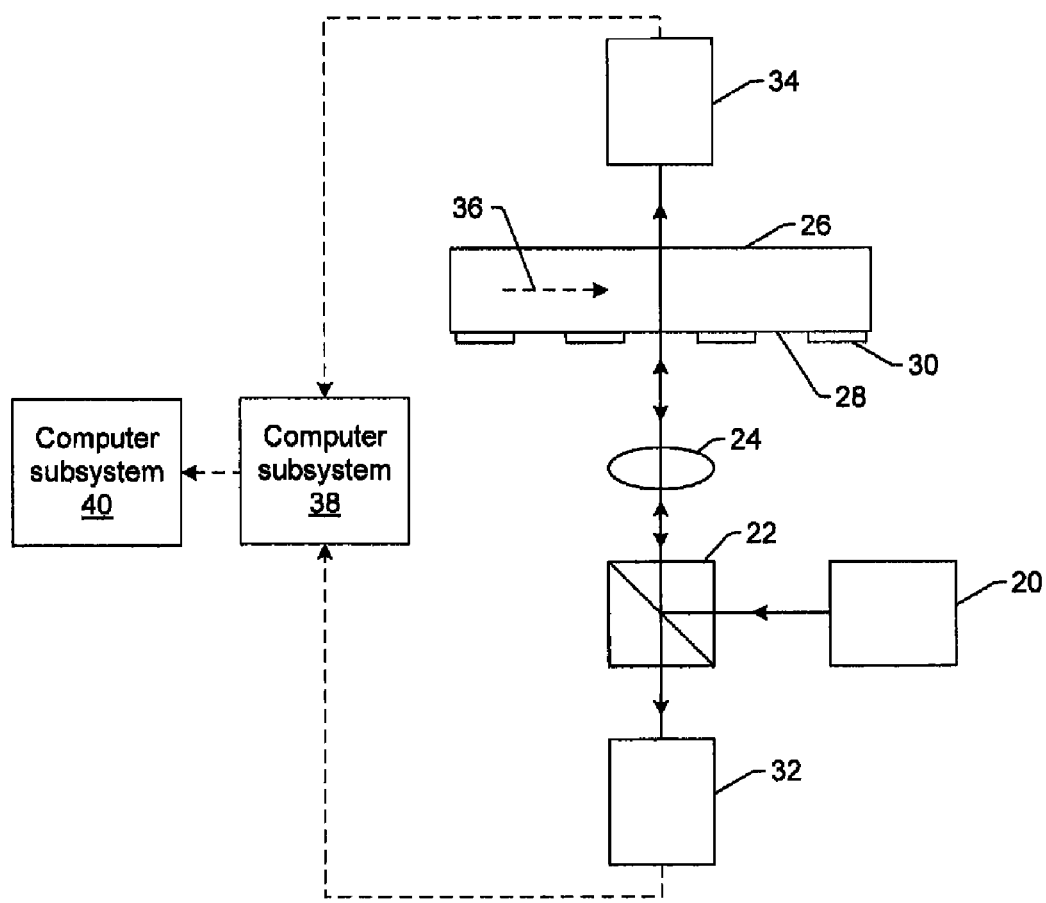
FIGS. 3-5 are schematic diagrams illustrating a side view of various embodiments of a system configured to classify defects detected on a reticle.

Another embodiment relates to a system configured to classify defects detected on a reticle. The system includes an inspection subsystem configured to detect a defect on a reticle. The inspection subsystem is also configured to acquire an image of at least a portion of the reticle in which the defect is located. One embodiment of such a system is shown in FIG. 3. The inspection subsystem included in the system shown in FIG. 3 includes light source 20. Light source 20 may include any suitable light source. Light generated by light source 20 is directed to beam splitter 22. Beam splitter 22 is configured to direct the light from the light source to lens 24. Beam splitter 22 may include any suitable beam splitter known in the art. Lens 24 may include any suitable refractive optical element known in the art. Lens 24 may also be replaced with one or more refractive optical elements and/or one or more reflective optical elements. Lens 24 is configured to direct the light from the beam splitter to reticle 26 at a substantially normal angle of incidence. As shown in FIG. 3, the light may be directed by lens 24 to surface 28 of reticle 26 on which patterned features 30 are formed.

Light directed to reticle 26 by lens 24 that is reflected from reticle 26 may pass through lens 24 and beam splitter 22 to detector 32. Detector 32 is configured to detect the light reflected from the reticle and is configured to generate output responsive to the reflected light. Detector 32 may include any suitable detector known in the art. The output generated by detector 32 may include any suitable output such as image data, images, etc. Light directed to reticle 26 that is transmitted by reticle 26 may be detected by detector 34. Detector 34 is configured to detect the light transmitted by the reticle and is configured to generate output responsive to the transmitted light. Detector 34 may include any suitable detector known in the art. The output generated by detector 34 may include any suitable output such as image data, images, etc.

Light reflected from and transmitted by the reticle may be detected as the light is directed to the reticle and while the reticle is moved (e.g., in a direction shown by arrow 36). For example, the inspection subsystem may include a mechanism (not shown) such as a stage or reticle handler that is configured to move the reticle while light is being directed to the reticle and while light reflected from and transmitted by the reticle is being detected. In this manner, the inspection subsystem may be configured to scan the reticle.

The inspection subsystem may also include computer subsystem 38. The computer subsystem may be coupled to detectors 32 and 34 such that the computer subsystem can receive the output generated by the detectors. For example, the computer subsystem may be coupled to the detectors by transmission media as shown by the dashed lines in FIG. 3. The transmission media may include any suitable transmission media known in the art. The computer subsystem may be configured to detect defects on the reticle. For example, the computer subsystem may be configured to use the output generated by the detectors and any suitable defect detection algorithm and/or method to detect defects on the reticle. In addition, the computer subsystem may be configured to acquire an image of at least a portion of the reticle in which a defect is located. The computer subsystem may acquire images of at least portions of the reticle corresponding to locations of defects on the reticle in any suitable manner. In this manner, the inspection subsystem is configured to detect a defect on a reticle and to acquire an image of at least a portion of the reticle in which the defect is located. The inspection subsystem may include any other suitable elements known in the art. In addition, the inspection subsystem may be further configured as described herein.

It is noted that FIG. 3 is provided to generally illustrate one configuration of an inspection subsystem that may be included in the system embodiments described herein. Obviously, the inspection subsystem configuration described herein may be altered to optimize the performance of the inspection subsystem as is normally performed when designing a commercial reticle inspection system. In addition, the systems described herein may be implemented using an existing reticle inspection system (e.g., by adding functionality described herein to an existing reticle inspection system) such as the TeraScan and TeraScanHR systems. For some such systems, the methods described herein may be provided as optional functionality of the reticle inspection system (e.g., in addition to other functionality of the reticle inspection system). Alternatively, the system described herein may be designed "from scratch" to provide a completely new system.

The system also includes computer subsystem 40 configured to generate a simulated image that illustrates how at least the portion of the reticle will print on a wafer using the image. Computer subsystem 40 may be coupled to computer subsystem 38 of the inspection subsystem in any suitable manner such that computer subsystem 40 can acquire and use the images acquired by computer subsystem 38. In addition, or alternatively, computer subsystem 40 may be coupled to a storage medium (not shown in FIG. 3) in which computer subsystem 38 stores the acquired images such that computer subsystem 40 can acquire and use those images. Computer subsystem 40 may be configured to generate a simulated image that illustrates how at least the portion of the reticle will print on the wafer using the image according to any of the embodiments described herein. In addition, the computer subsystem can include any suitable hardware and/or software that can be configured to perform such simulations.

The computer subsystem is also configured to determine an impact that the defect will have on the performance of a device being fabricated on the wafer based on the simulated image. Computer subsystem 40 may be configured to determine the impact that the defect will have on the performance of the device according to any of the embodiments described herein. The computer subsystem may also include any suitable hardware and/or software that can be configured to simulate the performance of the device according to any of the embodiments described herein and to determine the impact based on the simulated performance of the device as described herein. The performance of the device may include any performance of the device described herein. In addition, the computer subsystem is configured to assign a classification to the defect based on the impact. The computer subsystem may be configured to assign a classification to the defect according to any of the embodiments described herein. In addition, the computer subsystem may include any suitable hardware and/or software that can be configured to assign the classification to the defect according to any of the embodiments described herein. The classification assigned to the defect may include any of the classifications described herein. Furthermore, computer subsystem 38 may be configured as described above with respect to computer subsystem 40. For example, computer subsystem 38 may be configured to perform some or all of the step(s) that computer subsystem 40 may be configured to perform. In this manner, the system may or may not include computer subsystem 40.

The computer subsystems may be further configured as described herein. For example, the computer subsystems may be configured to perform any step(s) of any embodiment(s) described herein. In addition, the system shown in FIG. 3 may be further configured as described herein. For example, the system may be further configured to perform any step(s) of any method embodiment(s) described herein.

Figure 4:
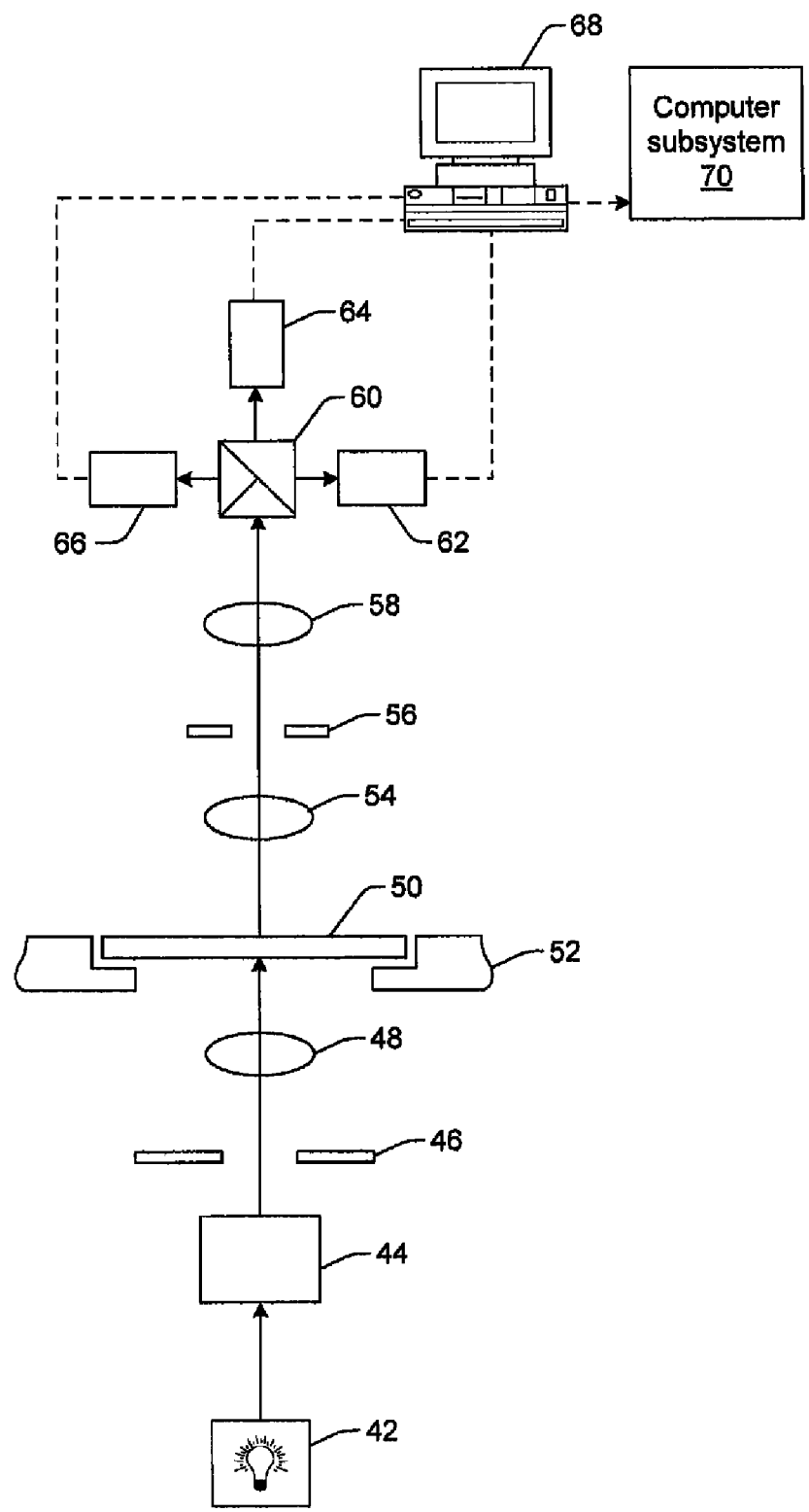

An additional embodiment relates to another system configured to classify defects detected on a reticle. The system includes an inspection subsystem configured to acquire an image that illustrates how at least a portion of the reticle prints or will print on a wafer. A defect detected on the reticle is located in the portion of the reticle. One such embodiment of a system is shown in FIG. 4. The inspection subsystem included in the system shown in FIG. 4 includes an illumination subsystem and a collection subsystem as described in more detail herein. The illumination subsystem includes light source 42. Light source 42 may be a coherent light source such as a laser. The light source may be configured to emit monochromatic light having a wavelength of about 248 nm, about 193 nm, about 157 nm, or another ultraviolet wavelength. Alternatively, the light source may be configured to emit light having a range of wavelengths and may be coupled to a spectral filter (not shown). An example of a broadband light source that may be used as light source 42 includes, but is not limited to, a He—Xe arc lamp that generates light in the deep ultraviolet wavelength regime. In this manner, the light source and the filter may emit monochromatic light having a wavelength as described above. The light source and the filter may be configured such that different wavelengths of light may be emitted from the light source and the filter depending upon, for example, the type of reticle being inspected or imaged, the type of inspection or measurement being performed, or the image being acquired. The light source may also be configured to emit light other than ultraviolet light. In addition, the light source may be configured to emit light continuously or at various time intervals in pulses.

The illumination subsystem also includes a number of optical components coupled to the light source. For example, light from light source 42 may pass through homogenizer 44. Homogenizer 44 may be configured to reduce speckle of the light from the light source. The illumination subsystem also includes aperture 46. Aperture 46 may be an adjustable numerical aperture (NA). For example, the aperture may be coupled to a control mechanism (not shown) that may be configured to mechanically alter the aperture depending upon a control signal received from a user or from program instructions received from a program recipe being run on the system. In this manner, the light may have various partial coherence factors, a. For example, aperture 46 may be altered to adjust a pupil of condenser lens 48. The pupil of the condenser lens controls the NA of the system. As the pupil of the condenser lens is reduced, coherence of the illumination increases thereby decreasing the value of σ. The value of a may be expressed as the ratio of the NA of the condenser lens to the NA of the objective lens. Exposure systems may have a value of σ in a range between about 0.3 to about 0.9. Therefore, aperture 46 may be altered such that the inspection subsystem has a value of σ between about 0.3 and about 0.9. The value of a may be altered depending upon the features being printed onto a wafer. For example, a higher value for a may be used if the reticle includes lines and spaces than if the reticle includes contact holes. The control mechanism may also be configured to alter the aperture to provide annular or off-axis illumination. The aperture may also be configured to provide other types of illumination such as quadrapole or dipolar illumination. The aperture may be further configured to alter a shape of the beam of light. For example, the aperture may be a diffraction optical element or an apodization aperture.

The illumination subsystem may also include a number of additional optical components (not shown). For example, the illumination subsystem may also include a telescope configured to alter the beam diameter of the light. In addition, the illumination subsystem may include one or more relay lenses, additional lenses such as a field lens, folding mirrors, additional apertures, and beam splitters.

The illumination subsystem also includes condenser lens 48. Condenser lens 48 may be configured to alter a diameter of the light in the object (reticle) plane to approximately, or greater than, the field of view of the system. Light exiting the condenser lens may illuminate reticle 50 supported upon stage 52. The stage is configured to support the reticle by contacting the reticle proximate outer lateral edges of the reticle. An opening in the stage is provided to allow light from the illumination subsystem to illuminate the reticle. Stage 52 may be configured to move the reticle such that an alignment of the reticle may be altered and such that light may scan across the reticle. Alternatively, the illumination subsystem may include a scanning element (not shown) such as an acousto-optical deflector or a mechanical scanning assembly such that the reticle may remain substantially stationary while the light is scanned across the reticle. Stage 52 may also be configured to move the reticle through focus thereby altering a focus setting of the system. The stage may also be coupled to an autofocusing device (not shown) that is configured to alter a position of the stage thereby altering a position of the reticle to maintain a focus setting of the inspection subsystem during image acquisition. Alternatively, an autofocusing device may be coupled to the objective lens to alter a position of the objective lens to maintain the focus setting during image acquisition.

The inspection subsystem also includes a number of optical components arranged to form a collection subsystem. For example, the collection subsystem includes objective lens 54. Light transmitted by the reticle is collected by objective lens 54. The collection subsystem also includes aperture 56 having an adjustable NA. The NA of aperture 56 may be selected such that light exiting the aperture has a selected magnification. Aperture 56 is positioned between objective lens 54 and lens 58, which may be configured as a tube lens. Light from lens 58 may be directed to beam splitter 60. Beam splitter 60 may be configured to direct the light to three detectors 62, 64, and 66. The collection subsystem may also include a number of additional optical components (not shown) such as a magnification lens. The magnification lens may be positioned between lens 58 and the beam splitter.

Detectors 62, 64, and 66 may be configured to form an image of the light transmitted by an illuminated portion of the reticle. Such an image may be referred to as an "aerial image." The detectors should also be sensitive to at least one of the wavelengths of light described above. The detectors, however, may also be sensitive to a range of wavelengths in the deep ultraviolet regime in addition to wavelengths in other regimes. The detectors may include, for example, charge-coupled device (CCD) cameras or time delay integration (TDI) cameras. The detectors may also have a one-dimensional or two-dimensional array of pixels.

Each of the three detectors may have a different focus setting. In other words, each of these detectors may be set at a different focal position. For example, detector 62 could be at 0 μm defocus, detector 64 could be at +0.2 μm defocus, and detector 66 could be at −0.2 μm defocus. In this manner, one detector may be substantially in focus, and the other two detectors may be out of focus in opposite directions with respect to the in-focus condition. Of course, these levels of defocus are only examples. Any suitable range of levels of defocus could be used, and such levels could be optimized empirically. In addition, it is not necessary to use a detector having 0 μm defocus, for example, and all of the detectors could be set at varying levels of positive defocus or at mixed levels of positive and negative defocus. In this manner, the three detectors may form images of the reticle at three different focus settings substantially simultaneously. In addition, the system may include any number of such detectors.

Alternatively, the collection subsystem may include only one detector configured to form an image of the reticle. The detector may have a focus setting approximately equal to a focus setting of an exposure system. In such a system, images of the reticle at different focus settings may be formed by forming a plurality of images of the reticle and altering the focus setting of the detector after each image is formed. In such a system, beam splitter 60 would not be necessary to split the light to multiple detectors.

The inspection subsystem may include a number of other components that are not shown in FIG. 4. For example, the inspection subsystem may include a load module, an alignment module, a handler such as a robotic transfer arm, and an environmental control module and may include any such components known in the art.

The inspection subsystem is configured to form an aerial image of the reticle using a set of exposure conditions. The exposure conditions may include, but are not limited to, wavelength of illumination, coherence of illumination, shape of the beam of illumination, NA, and focus settings. The set of exposure conditions may be selected to be substantially equivalent to exposure conditions used by an exposure system to print an image of the reticle onto a wafer. Therefore, an aerial image formed by the system may be substantially optically equivalent to an image of the reticle that would be projected on a wafer by the exposure system under the set of exposure conditions. In this manner, the inspection subsystem included in the system shown in FIG. 4 is configured to acquire an image that illustrates how at least a portion of a reticle will print on a wafer.

As described above, a defect detected on the reticle is located in at least the portion of the reticle for which an image is acquired. For example, the system may receive information about locations of defects detected on the reticle from a system that detected the defects on the reticle (not shown in FIG. 4) or a storage medium (not shown in FIG. 4) in which the information has been stored by a system that detected the defects on the reticle. The system that detected the defects on the reticle may include any of the systems described herein or any other suitable system. The storage medium may include any of the storage media described herein or any other suitable storage media known in the art. The system shown in FIG. 4 may be coupled to the system that detected the defects or the storage medium in which the information is stored in any suitable manner such that the information can be received by the system shown in FIG. 4. In this manner, the system shown in FIG. 4 may use the information about the defects detected on the reticle to acquire one or more images that illustrate how at least a portion of the reticle, in which at least a defect detected on the reticle is located, will print on a wafer.

However, the system shown in FIG. 4 may also acquire one or more images that illustrate how the entire reticle will print on the wafer. Different portions of the one or more images or different images that are acquired may then be used by the computer subsystem as described further herein.

The system shown in FIG. 4 may also be configured to detect defects on the reticle and then acquire an image that illustrates how at least a portion of the reticle, in which at least one defect is located, will print on the wafer. For example, as the reticle is illuminated, aerial image(s) may be detected at one or more of the three detectors. The inspection subsystem may also include computer subsystem 68. The computer subsystem may be coupled to detectors 62, 64, and 66 such that the computer subsystem can receive the aerial image(s) generated by the detectors. For example, the computer subsystem may be coupled to the detectors by transmission media as shown by the dashed lines in FIG. 4. The transmission media may include any suitable transmission media known in the art. The computer subsystem may be configured to detect defects on the reticle using the aerial image(s). For example, the computer subsystem may be configured to use the aerial image(s) generated by the detector(s) and any suitable defect detection algorithm and/or method to detect defects on the reticle. In addition, the computer subsystem may be configured to acquire an image of at least a portion of the reticle in which a defect is located. The computer subsystem may acquire images of at least portions of the reticle corresponding to locations of defects on the reticle in any suitable manner. In this manner, the inspection subsystem may be configured to detect a defect on a reticle and to acquire an image of at least a portion of the reticle in which the defect is located. The inspection subsystem may include any other suitable elements known in the art. In addition, the inspection subsystem may be further configured as described herein.

It is noted that FIG. 4 is provided herein to generally illustrate one configuration of an inspection subsystem that may be included in the system embodiments described herein. Obviously, the inspection subsystem configuration described herein may be altered to optimize the performance of the inspection subsystem as is normally performed when designing a commercial reticle inspection system. In addition, the systems described herein may be implemented using an existing aerial image reticle inspection system (e.g., by adding functionality described herein to an existing aerial image reticle inspection system). For some such systems, the methods described herein may be provided as optional functionality of the aerial image reticle inspection system (e.g., in addition to other functionality of the aerial image reticle inspection system). Alternatively, the system described herein may be designed "from scratch" to provide a completely new system.

The system also includes a computer subsystem configured to determine an impact that the defect will have on the performance of a device being fabricated on the wafer based on the image. For example, the system shown in FIG. 4 includes computer subsystem 70 that is configured to determine an impact that the defect will have on the performance of a device being fabricated on the wafer based on the image. Computer subsystem 70 may be coupled to computer subsystem 68 of the inspection subsystem in any suitable manner such that computer subsystem 70 can acquire and use the images acquired by computer subsystem 68. In addition, or alternatively, computer subsystem 70 may be coupled to a storage medium (not shown in FIG. 4) in which computer subsystem 68 stores the acquired images such that computer subsystem 70 can acquire and use those images. Computer subsystem 70 may be configured to determine the impact that the defect will have on the performance of the device according to any of the embodiments described herein. The computer subsystem may also include any suitable hardware and/or software that can be configured to simulate the performance of the device according to any of the embodiments described herein and to determine the impact based on the simulated performance of the device according to any of the embodiments described herein. The performance of the device may include any performance of the device described herein. The computer subsystem is also configured to assign a classification to the defect based on the impact. The computer subsystem may be configured to assign a classification to the defect according to any of the embodiments described herein. In addition, the computer subsystem may include any suitable hardware and/or software that can be configured to assign the classification to the defect according to any of the embodiments described herein. The classification may include any of the classifications described herein. Furthermore, computer subsystem 68 may be configured as described above with respect to computer subsystem 70. For example, computer subsystem 68 may be configured to perform some or all of the step(s) that computer subsystem 70 may be configured to perform. In this manner, the system may or may not include computer subsystem 70.

The computer subsystems shown in FIG. 4 may be further configured as described herein. For example, the computer subsystems may be configured to perform any step(s) of any embodiment(s) described herein. In addition, the system shown in FIG. 4 may be further configured as described herein. For example, the system may be configured to perform any step(s) of any method embodiment(s) described herein.

Figure 5:
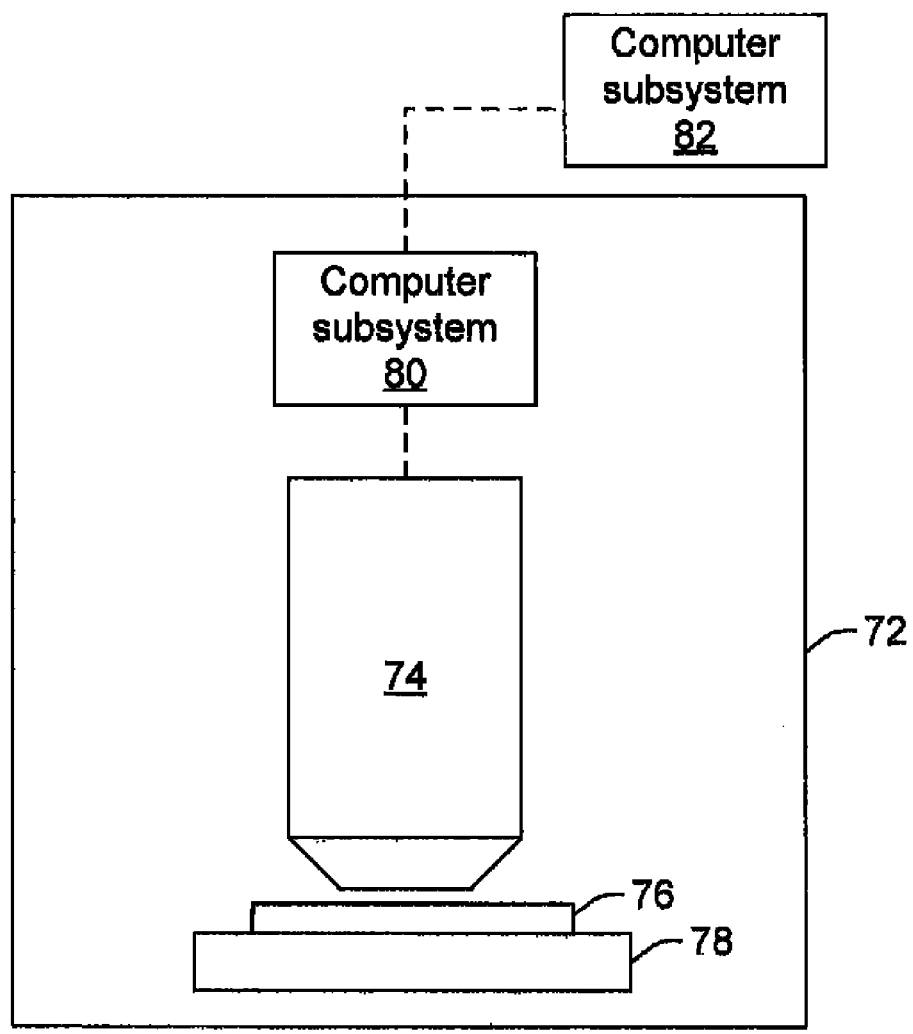

An additional embodiment relates to another system configured to classify defects detected on a reticle. The system includes an inspection subsystem configured to acquire an image that illustrates how at least a portion of the reticle prints or will print on a wafer. A defect detected on the reticle is located in the portion of the reticle. FIG. 5 illustrates one embodiment of such a system. As shown in FIG. 5, inspection subsystem 72 is configured to acquire an image that illustrates how at least a portion of the reticle (not shown in FIG. 5) prints on a wafer. For example, inspection subsystem 72 includes electron column 74. Electron column 74 is configured to direct electrons to wafer 76 and to detect electrons from the wafer. The electron column is also configured to generate output that is responsive to the electrons from the wafer that are detected by the electron column. Electron column 74 may have any suitable configuration known in the art. The output generated by the electron column may include any suitable output such as image data, images, etc. Wafer 76 has been printed using the reticle, defects on which are being classified by the system. In this manner, the image acquired by the inspection subsystem shown in FIG. 5 illustrates how at least a portion of the reticle prints on the wafer.

The inspection subsystem may also include stage 78 on which the wafer is located during imaging by the inspection subsystem. Stage 78 may include any suitable mechanical and/or robotic assembly and may be configured to move the wafer while the electrons are being directed to the wafer and detected from the wafer such that the inspection subsystem can scan the wafer.

As described above, a defect detected on the reticle is located in at least the portion of the reticle for which an image is acquired. For example, the system may receive information about locations of defects detected on the reticle from a system (not shown in FIG. 5) that detected the defects on the reticle or a storage medium (not shown in FIG. 5) in which the information has been stored by a system that detected the defects on the reticle. The system that detected the defects on the reticle may include any of the systems described herein or any other suitable system. The storage medium may include any of the storage media described herein or any other suitable storage media known in the art. The system shown in FIG. 5 may be coupled to the system that detected the defects or the storage medium in which the information is stored in any suitable manner such that the information can be received by the system shown in FIG. 5. A computer subsystem such as that described further herein may use the information about the defects detected on the reticle and information about how the reticle is printed on the wafer to determine locations of corresponding portions of the wafer. In this manner, the system shown in FIG. 5 may use the information about the defects detected on the reticle to acquire one or more images of at least one portion of the wafer that illustrate how at least a portion of the reticle, in which at least a defect detected on the reticle is located, prints on the wafer.

However, the system shown in FIG. 5 may also acquire one or more images that illustrate how the entire reticle prints on the wafer. For example, the system may acquire one or more images for an entire shot of the reticle printed on the wafer. Depending on the characteristics of the reticle, the entire shot may include a single die on the wafer, multiple die on the wafer, multiple fields on the wafer, etc. Different portions of the one or more images or different images that are acquired by the inspection subsystem may then be used by a computer subsystem as described further herein depending on the portions of the wafer corresponding to the images, the portions of the reticle corresponding to the portions of the wafer, and the locations of the defects on the reticle with respect to the portions of the reticle.

The system shown in FIG. 5 may also be configured to detect defects on the wafer, to determine if the defects detected on the wafer correspond to defects on the reticle, and to acquire an image of the wafer that illustrates how at least a portion of the reticle, in which at least one defect on the reticle is located, prints on the wafer. For example, the inspection subsystem may include computer subsystem 80. The computer subsystem may be coupled to electron column 74 such that the computer subsystem can receive the output generated by the electron column. For example, the computer subsystem may be coupled to a detector (not shown) of the electron column by transmission media as shown by the dashed line in FIG. 5. The transmission media may include any suitable transmission media known in the art. The computer subsystem may be configured to detect defects on the wafer using the output generated by the electron column. For example, the computer subsystem may be configured to use the output generated by the detector and any suitable defect detection algorithm and/or method to detect defects on the wafer. The computer subsystem may also be configured to determine if the defects detected on the wafer correspond to defects on the reticle. The computer subsystem may be configured to determine if the defects detected on the wafer correspond to defects on the reticle in any suitable manner. In addition, the computer subsystem may be configured to determine if the defects detected on the wafer correspond to defects on the reticle as described in commonly owned U.S. Pat. No. 6,902,855 to Peterson et al. and commonly owned U.S. patent application Ser. No. 10/883,372 filed Jul. 1, 2004 by Volk et al. published as U.S. Patent Application Publication No. 2005/0004774 on Jan. 1, 2005, which are incorporated by reference as if fully set forth herein. The embodiments described herein may be configured to perform any step(s) of any method(s) and/or system(s) described in this patent and this patent application. In addition, the computer subsystem may be configured to acquire an image of at least a portion of the wafer in which at least a portion of the reticle, in which a defect is located, has been printed. The computer subsystem may acquire images of at least portions of the wafer corresponding to locations of defects on the reticle in any suitable manner. In this manner, the inspection subsystem may be configured to detect a defect on a wafer, to determine if the defect corresponds to a defect on a reticle, and to acquire an image of at least a portion of the wafer in which the defect is located. The inspection subsystem may include any other suitable elements known in the art. In addition, the inspection subsystem may be further configured as described herein.

It is noted that FIG. 5 is provided herein to generally illustrate one configuration of an inspection subsystem that may be included in the system embodiments described herein. Obviously, the inspection subsystem configuration described herein may be altered to optimize the performance of the inspection subsystem as is normally performed when designing a commercial system. In addition, the systems described herein may be implemented using an existing wafer inspection system (e.g., by adding functionality described herein to an existing wafer inspection system) such as the eS3x series of tools that are commercially available from KLA-Tencor. For some such systems, the methods described herein may be provided as optional functionality of the wafer inspection system (e.g., in addition to other functionality of the wafer inspection system). Alternatively, the system described herein may be designed "from scratch" to provide a completely new system.

Furthermore, although the inspection subsystem is shown in FIG. 5 and described above as an electron beam inspection subsystem, the inspection subsystem may have any other configuration as long as the inspection subsystem can be configured and/or used to generate relatively detailed wafer inspection results that are suitable to drive the performance simulations described herein. For example, the inspection subsystem described above may be a local SEM or a relatively large scale electron beam inspection subsystem. Alternatively, the inspection subsystem shown in FIG. 5 may be replaced with an AFM. The AFM may have any suitable configuration known in the art. In addition, other configurations could be used in the system as long as they are accurate enough the drive the performance simulations described herein.

The system also includes a computer subsystem configured to determine an impact that the defect will have on the performance of a device being fabricated on the wafer based on the image. For example, the system shown in FIG. 5 includes computer subsystem 82 that is configured to determine an impact that the defect will have on the performance of a device being fabricated on the wafer based on the image. Computer subsystem 82 may be coupled to computer subsystem 80 of the inspection subsystem in any suitable manner such that computer subsystem 82 can acquire and use the images acquired by computer subsystem 80. In addition, or alternatively, computer subsystem 82 may be coupled to a storage medium (not shown in FIG. 5) in which computer subsystem 80 stores the acquired images such that computer subsystem 82 can acquire and use those images. Computer subsystem 82 may be configured to determine the impact that the defect will have on the performance of the device according to any of the embodiments described herein. The computer subsystem may also include any suitable hardware and/or software that can be configured to simulate the performance of the device according to any of the embodiments described herein and to determine the impact based on the simulated performance of the device according to any of the embodiments described herein. The performance of the device may include any performance of the device described herein. The computer subsystem is also configured to assign a classification to the defect based on the impact. The computer subsystem may be configured to assign a classification to the defect according to any of the embodiments described herein. In addition, the computer subsystem may include any suitable hardware and/or software that can be configured to assign the classification to the defect according to any of the embodiments described herein. The classification may include any of the classifications described herein. Furthermore, computer subsystem 80 may be configured as described above with respect to computer subsystem 82. For example, computer subsystem 80 may be configured to perform some or all of the step(s) that computer subsystem 82 may be configured to perform. In this manner, the system may or may not include computer subsystem 82.

The computer subsystems shown in FIG. 5 may be further configured as described herein. For example, the computer subsystems may be configured to perform any step(s) of any embodiment(s) described herein. In addition, the system shown in FIG. 5 may be further configured as described herein. For example, the system may be configured to perform any step(s) of any method embodiment(s) described herein.

Further modifications and alternative embodiments of various aspects of the invention may be apparent to those skilled in the art in view of this description. For example, methods and systems for classifying defects detected on a reticle are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A method for classifying defects detected on a reticle, comprising:
    determining an impact that a defect detected on a reticle will have on the performance of a device being fabricated on a wafer based on how at least a portion of the reticle prints or will print on the wafer and based on how at least another portion of the reticle prints or will print on the wafer, wherein the defect is located in the portion of the reticle, and wherein another defect is located in the other portion of the reticle; and
    assigning a classification to the defect based on the impact.

2. The method of claim 1, further comprising generating a simulated image that illustrates how at least the portion of the reticle will print on the wafer using an image of at least the portion of the reticle, wherein the image is generated by inspection of the reticle, and wherein said determining comprises determining the impact based on the simulated image.

3. The method of claim 1, further comprising generating an aerial image that illustrates how at least the portion of the reticle will print on the wafer, wherein the aerial image is generated by inspection of the reticle, and wherein said determining comprises determining the impact based on the aerial image.

4. The method of claim 1, further comprising generating an image of at least a portion of the wafer in which at least the portion of the reticle is printed, wherein the image is generated by inspection of the wafer, and wherein said determining comprises determining the impact based on the image.

5. The method of claim 1, wherein said determining comprises simulating the impact that the defect will have on the performance of the device.

6. The method of claim 1, wherein the performance of the device comprises one or more electrical characteristics of the device, one or more thermal characteristics of the device, or some combination thereof.

7. The method of claim 1, wherein said determining is performed online during inspection of the reticle.

8. The method of claim 1, further comprising determining if the defect is to be reported in inspection results for the reticle based on the classification assigned to the defect.

9. The method of claim 1, wherein said determining is performed offline after inspection of the reticle.

10. The method of claim 1, wherein said determining comprises determining the impact based on how at least the portion of the reticle prints or will print on the wafer and based on how at least a portion of an additional reticle prints or will print on the wafer, and wherein the reticle and the additional reticle are printed or will be printed on different layers of the wafer.

11. The method of claim 1, wherein the performance of the device comprises the performance of only a portion of the device.

12. The method of claim 1, wherein the performance of the device comprises the performance of the entire device.

13. The method of claim 1, further comprising determining if the defect should be reviewed based on the classification and not based on information about the portion of the reticle in which the defect is located.

14. The method of claim 1, further comprising determining if the defect should be repaired based on the classification and not based on information about the portion of the reticle in which the defect is located.

15. The method of claim 1, further comprising determining if the reticle should be discarded based on the classification and not based on information about the portion of the reticle in which the defect is located.

16. The method of claim 1, wherein said determining and said assigning are performed for all defects detected on the reticle.

17. The method of claim 1, further comprising determining if defects detected on the reticle print or will print on the wafer based on how at least portions of the reticle corresponding to locations of the defects print or will print on the wafer, wherein said determining and said assigning are performed for only defects that print or will print on the wafer.

18. A system configured to classify defects detected on a reticle, comprising:
   an inspection subsystem configured to detect a defect on a reticle and to acquire an image of at least a portion of the reticle in which the defect is located, wherein another defect is located in another portion of the reticle; and
   a computer subsystem configured to generate a simulated image that illustrates how at least the portion of the reticle will print on a wafer using the image, determine an impact that the defect will have on the performance of a device being fabricated on the wafer based on the simulated image and based on how at least the other portion of the reticle prints or will print on the wafer, and assign a classification to the defect based on the impact.

19. A system configured to classify defects detected on a reticle, comprising:
   an inspection subsystem configured to acquire an image that illustrates how at least a portion of a reticle prints or will print on a wafer, wherein a defect detected on the reticle is located in the portion of the reticle, and wherein another defect is located in another portion of the reticle; and
   a computer subsystem configured to determine an impact that the defect will have on the performance of a device being fabricated on the wafer based on the image and based on how at least the other portion of the reticle prints or will print on the wafer and to assign a classification to the defect based on the impact.

* * * * *